US005597895A

United States Patent [19]
Gaynor et al.

[11] Patent Number: 5,597,895
[45] Date of Patent: Jan. 28, 1997

[54] TRANSDOMINANT TAT MUTANTS AND USES THEREOF

[75] Inventors: Richard B. Gaynor, Dallas, Tex.; Joseph A. Garcia, Santa Monica, Calif.; David Harrich, Carrollton, Tex.

[73] Assignee: Board of Regents, University of Texas System, Austin, Tex.

[21] Appl. No.: 910,867

[22] Filed: Jul. 2, 1992

Related U.S. Application Data

[63] Continuation-in-part of Ser. No. 788,266, Nov. 5, 1991, Pat. No. 5,350,835.

[51] Int. Cl.$^6$ .......................... C07K 14/15; C07K 14/155
[52] U.S. Cl. ........................ 530/324; 530/329; 530/330; 530/350; 435/320.1
[58] Field of Search ............................. 435/320.1, 69.1; 530/324, 329, 330, 350; 935/66, 71, 52, 56

[56] References Cited

U.S. PATENT DOCUMENTS 5,350,835  9/1994  Gaynor et al. ........................... 530/358

OTHER PUBLICATIONS

Li, Ching et al., "Cloning of a Cellular Factor, Interleukin Binding Factor, That Binds to NFAT–Like Motifs in the Human Immunodeficiency Virus Long Terminal Repeat," *Proc. Natl. Acad. Sci. USA*, 88:7739–7743, 1991, published in USA.

Calnan, Barbara J. et al., "Analysis of Arginine–Rich Peptides from the HIV Tat Protein Reveals Unusual Features of RNA–Protein Recognition," *Genes and Development*, 5:201–210, 1991, published in USA.

Modesti, Nidia et al., "Trans–Dominant Tat Mutants with Alterations in the Basic Domain Inhibit HIV–1 Gene Expression," *The New Biologist*, 3(8):759–768, 1991, published in USA.

Pearson, Lori et al., "A Transdominant Tat Mutant That Inhibits Tat–Induced Gene Expression from the Human Immunodeficiency Virus Long Terminal Repeat," *Proc. Natl. Acad. Sci. USA*, 87:5079–5083, 1990, published in USA.

Brake, David A. et al., "Characterization of Murine Monoclonal Antibodies to the Tat Protein from Human Immunodeficiency Virus Type 1," *Journal of Virology*, 64(2):962–965, 1990, published in USA.

Dayton, Andrew I. et al., "The Trans–Activator Gene of the Human T Cell Lymphotropic Virus Type III Is Required for Replication," *Cell*, 44:941–947, 1986, published in USA.

Feng, Sandy and Holland, Eric C., "HIV–1 Tat Trans–Activation requires the Loop Sequence within Tar," *Nature*, 334:165–167, 1988, published in Great Britain.

Fisher, Amanda G., et al., "The Trans–Activator Gene of HTLV–III Is Essential for Virus Replication," *Nature*, 320:367–371, 1986, published in Great Britain.

Frankel, Alan D. et al., "Tat Protein from Human Immunodeficiency Virus Forms a Metal–Linked Dimer," *Science*, 240:70–73, 1988, published in USA.

Friedman, Alan D. et al., "Expression of a Truncated Viral Trans–Activator Selectively Impedes Lytic Infection by Its Cognate Virus," *Nature*, 335:452–454, published in Great Britain.

Garcia, Joseph A. et al., "Functional Domains required for Tat–Induced Transcriptional Activation of the HIV–1 Long Terminal Repeat," *The EMBO Journal*, 7 (10):3143–3147, 1988, published in Great Britian.

Garcia, Joseph A. et al., "Human Immunodeficiency Virus Type 1 LTR TATA and TAR Region Sequences Required for Transcriptional Regulation," *The EMBO Journal*, 8(3):765–778, 1989, published in Great Britian.

Glenn, Gary M. and Ricciardi, Robert P., "An Adenovirus Type 5 E1A Protein with a Single Amino Acid Substitution Blocks Wild–Type E1A Transactivation," *Molecular and Cellular Biology*, 7(3):1004–1011, published in USA.

Gorman, Cornelia M. et al., "Recombinant Genomes Which Express Chloramphenicol Acetyltransferase in Mammalian Cells," *Molecular and Cellular Biology*, 2(9):1044–1051, 1982, published in USA.

Harrich, David et al., "TAR Independent Activation of the Human Immunodeficiency Virus in Phorbol Ester Stimulated T Lymphocytes," *The EMBO Journal*, 9:13):4417–4434, 1990, published in Great Britain.

Hauber, Joachim et al., "Mutational Analysis of the Conserved Basic Domain of Human Immunodeficiency Virus Tat Protein," *Journal of Virology*, 63(3):1181–1187, 1989, published in USA.

Jones, Katherine A. et al., "Activation of the AIDS Retrovirus Promoter by the Cellular Transcription Factor, Sp1," *Science*, 232:755–759, 1986, published in USA.

Malim, Michael H. et al., "Functional Dissection of the HIV–1 Rev Trans–Activator–Derivation of a Trans–Dominant Repressor of Rev Function," *Cell*, 58:205–214, 1989, published in USA.

Rice, Andrew P. and Carlotti, Franco, "Mutational Analysis of the Conserved Cysteine–Rich Region of the Human Immunodeficiency Virus Type–1 Tat Protein," *Journal of Virology*, 64(4):1864–1868, 1990, published in USA.

(List continued on next page.)

Primary Examiner—Mindy Fleisher
Assistant Examiner—David Guzo
Attorney, Agent, or Firm—Akin, Gump, Strauss, Hauer & Feld, L.L.P.

[57] ABSTRACT

Transdominant HIV tat substitution and truncated gene mutants of 72 amino acid residues or less are disclosed. The mutated genes encode mutant Tat proteins which are capable of inhibiting the expression of the HIV-1 virus in the presence of an equimolar concentration of the wild type Tat protein in vitro. Therapeutic agents which include fused protein forms of the mutant proteins are also disclosed, as well as methods of preparing and using the therapeutic agents in the treatment of HIV infection and HIV-related injections in an animal. Recombinant vectors which express the mutant HIV Tat proteins described are also disclosed, as well as cell lines which product high yields of the mutant HIV.

11 Claims, 11 Drawing Sheets

OTHER PUBLICATIONS

Rosen, Craig A. et al., "The Location of Cis–Acting Regulatory Sequences in the Human T Cell Lymphotropic Virus Type III (HTLV–III/LAV) Long Terminal Repeat," *Cell*, 41:813–823, 1985, published in USA.

Ruben, Steven et al., "Structural and Functional Characterization of Human Immunodeficiency Virus Tat Protein," *Journal of Virology*, 63(1):1–8, 1989, published in USA.

Sadaie, M. Reza et al., "Site–Directed Mutagenesis of Two Trans–Regulatory Genes (tat–III, trs) of HIV–1," *Science*, 239:910–913, 1988, published in USA.

Selby, Mark J. et al., "Structure, Sequence, and Position of the Stem–Loop in tar Determine Transcriptional Elongation by tat Through the HIV–1 Long Terminal Repeat," *Genes & Development*, 3:547–558, 1989, published in USA.

Siomi, Haruhiko et al., "Effects of a Highly Basic Region of Human Immunodeficiency Virus Tat Protein on Nucleolar Localization," *Journal of Virology*, 64(4):1803–1807, 1990, published in USA.

Wu, Foon et al., "tat Regulates Binding of the Human Immunodeficiency Virus Trans–Activating Region RNA Loop–Binding Protein TRP–185," *Genes & Development*, 5:2128–2140, 1991, published in USA.

Mann, David A. and Frankel, Alan D., "Endocytosis and Targeting of Exogenous HIV–1 Tat Protein," *The EMBO Journal*, 10(7):1733–1739, 1991, published in Great Britain.

Elroy–Stein, Orna et al., "Cap–Independent Translation of mRNA Conferred by Encephalomyocarditis Virus 5' Sequence Improves the Performance of the Vaccinia Virus/Bacteriophage T7 Hybrid Expression System," *Proc. Natl. Acad. Sci. USA.*, 86:6126–6130, 1989, published in USA.

Templeton, Dennis J., "Nuclear Binding of Purified Retinoblastoma Gene Product Is Determined by Cell Cycle–Regulated Phosphorylation," *Molecular and Cellular Biology*, 12(2):435–443, 1992, published in USA.

Marciniak, Robert A. et al., "HIV–1 Tat Protein Trans–Activates Transcription in Vitro," *Cell*, 63:791–802, 1990, published in USA.

Gaynor, Richard et al., "Specific Binding of a HeLa Cell Nuclear Protein to RNA Sequences in the Human Immunodeficiency Virus Transactivating Region," *Proc. Natl. Acad. Sci. USA*, 86:4858–4862, 1989, published in USA.

Hauber, Joachim et al., "Trans–Activation of Human Immunodeficiency Virus Gene Expression Is Mediated by Nuclear Events," *Proc. Natl. Acad. Sci. USA*, 84:6364–6368, 1987, published in USA.

Selby, Mark J. and Peterlin, B. Matija, "Trans–Activation by HIV–1 Tat via a Heterologous RNA Binding Protein," *Cell*, 62:769–776, 1990, published in USA.

Weeks, Kevin M. et al., "Fragments of the HIV–1 Tat Protein Specifically Bind TAR RNA," *Science*, 249:1281–1285, 1990, published in USA.

Gentz, Reiner et al., "Bioassay for Trans–Activation Using Purified Human Immunodeficiency Virus Tat–Encoded Protein: Trans–Activation Requires mRNA Synthesis," *Proc. Natl. Acad. Sci USA*, 86:821–824, 1989, published in USA.

Gaynor, R. B. et al., "Repeated B Motifs in the Human Immunodeficiency Virus Type I Long Terminal Repeat Enhancer Region Do Not Exhibit Cooperative Factor Binding," *Proc. Natl. Acad. Sci. USA*, 85:9406–9410, 1988, published in USA.

```
MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Phe His Cys Tyr Ala Cys Phe Thr Arg Lys Gly Leu
TGT AAC AAT TGC TAT TGT AAA AAG TGT TTT CAT TGC TAC GCG TGT TTC ACA AGA AAA GGC TTA

A    B    C
                                                   ┌─────────────┐
                                                   │            ┌─┼──────┐
                                         ┌─────────┼───┐      ┌─┼─┼──┐   │
Gly Ile Ser Tyr Gly Arg Lys Lys Arg Arg │Gln  Arg Arg│ Arg │Ala│ Pro Gln Asp Ser Gln Thr
GGC ATC TCC TAT GGC AGG AAG AAG CGG AGA│CAG  CGA AGA│ AGA │GCT│ CCT CAG GAC AGT CAG ACT
                                         └─────────┴───┘      └─┴─┘
                49   50  51   52   53    54    55   56    57   58

His Gln Ala Ser Leu Ser Lys Gln
CAT CAA GCT TCT CTA TCA AAG CAG TAA

FIG. 1
```

| MET | Glu | Pro | Val | Asp | Pro | Asn | Leu | Glu | Pro | Trp | Lys | His | Pro | Gly | Ser | Gln | Pro | Arg | Thr | Ala |
|---|---|---|---|---|---|---|---|---|---|---|---|---|---|---|---|---|---|---|---|---|
| ATG | GAG | CCA | GTA | GAT | CCT | AAT | CTA | GAG | CCC | TGG | AAG | CAT | CCA | GGA | AGT | CAG | CCT | AGG | ACT | GCT |

| Cys | Asn | Cys | Tyr | Cys | Lys | Lys | Cys | Cys | Phe | His | Cys | Tyr | Ala | Cys | Phe | Thr | Arg | Lys | Gly | Leu |
|---|---|---|---|---|---|---|---|---|---|---|---|---|---|---|---|---|---|---|---|---|
| TGT | AAC | AAT | TGC | TAT | TGT | AAA | AAG | TGT | TGC | TTT | CAT | TGC | TAC | GCG | TGT | TTC | ACA | AGA | AAA | GGC | TTA |

| Gly | Ile | Ser | Tyr | Gly | Arg | Lys | Lys | Gly | Gly | Ala | Gly | Gly | Gly | Ala | Pro | Gln | Asp | Ser | Gln | Thr |
|---|---|---|---|---|---|---|---|---|---|---|---|---|---|---|---|---|---|---|---|---|
| GGC | ATC | TCC | TAT | GGC | AGG | AAG | AAG | GGG | GGA | GCC | GGC | GGA | GGA | GCT | CCT | CAG | GAC | AGT | CAG | ACT |
|  |  |  |  |  |  | 49 | 50 | 51 | 52 | 53 | 54 | 55 | 56 | 57 | 58 |  |  |  |  |  |

| His | Gln | Ala | Ser | Leu | Ser | Lys | Gln |
|---|---|---|---|---|---|---|---|
| CAT | CAA | GCT | TCT | CTA | TCA | AAG | CAG | TAA |

FIG. 7A

*(tat 52/57) mutant*

| | | | | | | | | | | | |
|---|---|---|---|---|---|---|---|---|---|---|---|
| MET | Glu | Pro | Val | Asp | Pro | Asn | Leu | Glu | Pro | Trp | Lys | His | Pro | Gly | Ser | Gln | Pro | Arg | Thr | Ala |
| ATG | GAG | CCA | GTA | GAT | CCT | AAT | CTA | GAG | CCC | TGG | AAG | CAT | CCA | GGA | AGT | CAG | CCT | AGG | ACT | GCT |

| | | | | | | | | | | | |
|---|---|---|---|---|---|---|---|---|---|---|---|
| Cys | Asn | Asn | Cys | Tyr | Cys | Lys | Lys | Cys | Cys | Phe | His | Cys | Tyr | Ala | Cys | Phe | Thr | Arg | Lys | Gly | Leu |
| TGT | AAC | AAT | TGC | TAT | TGT | AAA | AAG | TGT | TGC | TTT | CAT | TGC | TAC | GCG | TGT | TTC | ACA | AGA | AAA | GGC | TTA |

| Gly | Ile | Ser | Tyr | Gly | Arg | Lys | Lys | Arg | Arg | Ala | Gly | Gly | Gly | Ala | Pro | Gln | Asp | Ser | Gln | Thr |
|---|---|---|---|---|---|---|---|---|---|---|---|---|---|---|---|---|---|---|---|---|
| GGC | ATC | TCC | TAT | GGC | AGG | AAG | AAG | CGG | AGA | GCC | GGC | GGA | GGA | GCT | CCT | CAG | GAC | AGT | CAG | ACT |
| | | | | 49 | 50 | 51 | 52 | 53 | 54 | 55 | 56 | 57 | 58 | | | | | | | |

| His | Gln | Ala | Ser | Leu | Ser | Lys | Gln |
|---|---|---|---|---|---|---|---|
| CAT | CAA | GCT | TCT | CTA | TCA | AAG | CAG | TAA |

FIG. 7B
(tat 54/57) mutant

```
MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Cys Phe His Cys Tyr Ala Cys Phe Thr Arg Lys Gly Leu
TGT AAC AAT TGC TAT TGT AAA AAG TGT TGC TTT CAT TGC TAC GCG TGT TTC ACA AGA AAA GGC TTA

Gly Ile Ser Tyr Gly Arg Lys Lys Arg Arg Gln  Gly Ala Gly Gly  Pro Gln Asp Ser Gln Thr
GGC ATC TCC TAT GGC AGG AAG AAG CGG AGA CAG  GGA GCC GGC GGT  CCT CAG GAC AGT CAG ACT
                49  50  51  52  53  54       55  56  57  58

His Gln Ala Ser Leu Ser Lys Gln
CAT CAA GCT TCT CTA TCA AAG CAG TAA
```

FIG. 7C
(tat 55/58) mutant

TRANSDOMINANT TAT MUTANTS AND USES THEREOF

The government has rights in the present invention as research relevant to the development thereof was supported by NIH grant #AI25288.

This application is a continuation-in-part of U.S. Ser. No. 07/788,266, filed Nov. 5, 1991, issuing as U.S. Pat. No. 5,350,835 on Sep. 27, 1994.

BACKGROUND OF THE INVENTION

1. Field of the Invention

The present invention relates to the field of viral proteins, particularly those proteins involved in HIV gene regulation and mutants thereof. The gene which encodes the viral factor is also related to the field of the present invention. Recombinant vectors and host cells including the gene for the new nucleic acid binding factor is also related to the present disclosure. The present invention also relates to the field of methods for regulating the expression of cellular and viral genes, particularly HIV gene expression, and to methods of treatment, and therapeutic agents for treating acquired immunodeficiency disease and other HIV related diseases or symptoms incident an HIV or AIDS infection.

2. Background of the Related Art

The regulation of HIV-1 gene expression is dependent on a number of cis-acting elements located in the LTR. Both DNA and RNA elements in the HIV-1 LTR serve as binding sites for cellular factors. In addition, viral regulatory proteins such as Tat and rev are involved in the activation of gene HIV-1 expression. The mechanisms by which cellular factors interact with Tat and rev to increase HIV-1 gene expression are not understood.

The human immunodeficiency virus (HIV) is the causative agent of AIDS.[2,26] In common with other retroviruses[10], HIV contains two long terminal repeats (LTRs) and three conserved genes, gag, pol, and env. It also contains a number of critical regulatory genes including tat and rev which, in conjunction with cellular polymerases and transcription factors, are necessary for the activation of viral gene expression.[7,14,21] Once HIV-1 integrates into the host cell genome, its gene expression is regulated by cellular transcription factors in a manner similar to that of endogenous cellular genes.[10] Unlike cellular genes, unique features in the DNA and RNA regulatory regions of the HIV-1 LTR make it a target for the viral transactivator protein, Tat. The activities of several of the cellular transcription factors which bind to the HIV-1 LTR are altered by parameters such as activation or differentiation of lymphocytes or macrophages, the action of lymphokines, and alterations of signal transduction pathways.[12,35] Thus, HIV is subject to many of the same regulatory signals that are important in controlling cellular gene expression.

A variety of viral transactivators including the adenovirus E1A, cytomegalovirus immediate early, and the human T-cell leukemia virus tax proteins are able to activate HIV-1 gene expression.[6,32] These proteins activate HIV-1 through different regulatory elements including the TATA box, USF binding site, and NF-kB sites respectively.[6,32] In contrast to these viral transactivator proteins whose activity is relatively permissive, activation by the Tat protein is specific for HIV. Disruption of the tat gene prevents viral replication indicating its essential role in the HIV-1 life cycle.[14,21] The Tat protein is known to possess at least three functional domains.[28] These include an amino-terminal activation domain, a cysteine-rich domain which may function in dimerization, and a basic domain which is important in nuclear localization and RNA binding.[8,9,11,15,16,28] Despite knowledge of these details, the mechanism of Tat activation remains open to question, and thus an identification of potential interactions between Tat and cellular factors is important for understanding Tat function.

A number of cis-acting regulatory elements in the HIV-1 LTR are critical for basal and Tat-induced gene expression. These include the enhancer, SP1[38,45], TATA28[29,46] and TAR elements[3,19,29,44]. Each of these elements serves as a binding site for cellular transcription factors. Though the SP1 and TATA elements influence the basal level of HIV-1 gene expression, they also play a role in determining the level of activation by the transactivator protein Tat.[45] The TAR element which forms a stable stem-loop RNA structure extending from +1 to +60 is critical for Tat activation.[3,19,24,44] A number of studies using fusions of Tat to other known DNA or RNA binding proteins indicate that Tat is able to activate HIV-1 gene expression when bound to either DNA or RNA.[41,45] Thus it is likely that factors binding to both DNA and RNA regulatory elements influence the degree of Tat activation.

Mutagenesis has localized a region of TAR RNA between +18 and +44 as an essential element for activation by Tat.[3-5,13,19,29,42] Several elements in this RNA region including the bulge (+23/+25), the loop (+30/+35), and the stem structure are required for complete Tat-activation.[3,5,13,19,29,42] The function of the stem structure is likely to maintain the position of the bulge and loop structures. The bulge region in TAR RNA serves as the binding site for Tat though the loop sequences also influence Tat binding.[8,9,11,16] In addition, cellular factors are also capable of binding to the bulge sequences. The interaction between Tat and the TAR RNA bulge is very specific in that a change of one nucleotide at +23 in the bulge is sufficient to disrupt Tat binding.[8,9,11,16] The basic domain of Tat is necessary and sufficient for binding to the TAR RNA bulge.[8,9,11,16] Extensive mutagenesis of the Tat protein indicates that arginine residues at positions 52 and 53 of Tat are especially critical for interacting with phosphate groups in the TAR RNA bulge.[9] The Tat binding to the TAR RNA bulge is thus highly specific and of great affinity.

In contrast to the bulge which binds a viral protein, the loop sequences serve as a binding site for cellular factors that may cooperate with Tat in activating HIV-1 gene expression.[30,31] Fractionation of HeLa nuclear extract and gel retardation and UV crosslinking using TAR RNA probes indicate that two different cellular proteins p68 and TRP-185 bind to the TAR RNA loop sequences. TRP-185 is a ubiquitously expressed 185kDa protein whose binding to TAR RNA is regulated by additional cofactor proteins. These cofactors likely function by post-translational modification of TRP-185 i.e., phosphorylation. TRP-185 binding to TAR RNA requires wild-type loop sequences and an intact bulge structure. The binding of TRP-185 to TAR RNA, unlike that of Tat, is not markedly influenced by the primary sequences of the bulge region. Both Tat and TRP-185 activate HIV-1 LTR gene expression in in vitro transcription assays, but whether these proteins directly interact is not known. These results indicate that Tat activation via the TAR element may require interactions between Tat and cellular transcription factors.

Activation of the HIV-1 LTR by Tat proteins with an altered basic domain has previously been demonstrated to be strongly dependent on the concentration of transfected DNA (Ruben et al., 1989; Hauber et al., 1989). However, how this finding relates to the overall activation of the HIV-1 LTR remains to be determined.

It is critical to determine how Tat modulates the transcriptional apparatus to increase HIV-1 gene expression. Tat stimulates steady state RNA levels synthesized from the HIV-1 LTR approximately 20 to 50-fold. Nuclear run-on experiments using the HIV-1 LTR indicate that Tat stimulates transcriptional initiation. However another effect of Tat function is seen when nascent RNA is measured at various positions downstream of the HIV-1 LTR initiation site in both the presence and absence of Tat.[18] Though several studies demonstrate an increased number of RNA molecules synthesized from proximal portions of the HIV-1 LTR (near the initiation site) in the presence of Tat, the predominant effect of Tat appears to be a marked increase in the level of RNA synthesized at promoter distal sites (between 500 to 1000 nucleotides from the initiation site).[18] In vitro analysis of Tat transactivation also supports an effect on transcriptional elongation. The ability of Tat to increase the number of elongated transcripts may be one explanation for the decrease in the number of short transcripts which are synthesized from the HIV-1 LTR in the absence of Tat. These short transcripts terminate around +60 in the TAR element and may reflect the products of poorly processive transcription complexes. Thus, Tat may function at multiple steps in the transcriptional pathway to increase both the initiation and elongation of transcripts from the HIV LTR.

Mutations in a number of HIV-1 genes including tat (Pearson et al. (1990)), rev ((Malin et al. (1989)), and gag (Trono et al. (1989)) result in proteins with a dominant negative or transdominant phenotype that interfere with the function of the corresponding wild-type proteins. Recently, a Δtat mutation has been described by the present inventors. The Δtat mutant gene therein encoded a 54 amino acid length HIV protein having truncated basic domain (Pearson et al. (1990)). The "basic domain" of the tat gene includes 9 amino acids and is defined by amino acid residues 49–57 of the first 72 amino acids encoding the Tat protein (Pearson et al. (1990)). Three (3) of the amino acid residues of the basic domain of the HIV Tat protein were eliminated in the Δtat to provide the final protein product, leaving six (6) of the residues of the basic domain unchanged. While the Δtat-encoded protein was found to inhibit Tat activation of the HIV-1 LTR when the vector expressing it was present in a 5- to 30-fold molar excess over a vector expressing the wild-type Tat, the mutations were not found to result in a transdominant phenotype.

Further characterization of the precise mechanisms controlling HIV gene expression in regard to the role of the "basic domain" of the tat gene has not been explored, despite the impact such would have in providing more potent and effective therapeutic agents for treating HIV infections.

Previous data have demonstrated that Tat protein is capable of entering cells in culture when added to the tissue culture media.[23] Though the mechanism of entry is not understood it appears to be a result of endocytosis. To develop transdominant Tat mutant peptides for potential therapeutic use it would be important to develop transdominant mutants of minimal size. This is due to the fact that the amount of partial products and the yield of peptides decrease significantly as their size is increased. A construct which encoded a peptide capable of providing defective activation of HIV LTR gene expression and an ability to antagonize wild-type Tat function, and which was of sufficiently small size to optimize partial product and peptide yield would enable the production of an entirely new class of therapeutic agents used in the treatment and potential cure of HIV infections.

SUMMARY OF THE INVENTION

Genetic mutants of the Tat protein have been constructed which are able to antagonize the function of the corresponding wild-type protein. These transdominant mutant proteins, provide powerful tools for both investigating the mechanisms by which these regulatory proteins activate HIV-1 gene expression and providing potentially potent anti-HIV therapeutic agents. These mutant proteins more specifically, according to methods set forth by the present inventors, may be employed as therapeutic agents to inhibit HIV-1 growth.

The inventors laboratory has successfully constructed a series of transdominant Tat mutant proteins which inhibit wild-type Tat function. These mutants may be introduced into HIV-1 infected cells to inhibit viral gene expression and to even further investigate the mechanisms by which they antagonize wild-type Tat function.

The scope of the present invention includes:

(1) Tat transdominant mutants which inhibit wild-type Tat function;

(2) the construction of HIV-1 proviruses containing transdominant tat mutants for use as vectors to inhibit HIV-1 gene expression;

(3) the production of wild-type and transdominant Tat mutant proteins in both bacterial and vaccinia expression systems for in vitro and in vivo studies of their effects on HIV-1 gene expression;

(4) the definition of the interaction which occurs between common cellular proteins with wild-type and transdominant Tat proteins in the determination of cellular targets of Tat action; and (5) the proposition of unique potentially useful compositions and methods for the treatment of HIV and related infections.

With the work disclosed herein regarding the Tat mutant protein, the present inventors postulate that cell lines which stably express the specific transdominant mutant Tat protein can be made "immune" to subsequent viral, particularly HIV-1, infection. The present invention therefore proposes transdominant mutant genes to provide a method for "intracellular immunization" as a means of preventing viral infection.

The present invention provides potent transdominant Tat mutants and characterizes the mechanism by which these mutants inhibit tat gene activation of the HIV-1 LTR.

The inventors' previous mutagenesis of the tat gene has provided for the identification of a truncated tat mutant known as Δtat, which inhibited wild-type tat gene activation of the HIV-1 LTR in transfection assays (*Proc. Natl. Acad. Sci.*, 87:5079–5083 (1991)). This inhibition required a 5 to 20-fold molar excess of Δtat over wild-type tat and was specific for the HIV-1 LTR. The transdominant phenotype of this mutant, which resulted from a truncation in the basic domain of Tat at amino acid 54, was eliminated by second site mutations in either the amino-terminus or cysteine region.

The present work of the inventors provides for the construction of transdominant substitution Tat mutants which have the surprising and unexpected effect of inhibiting wild-type tat gene function at equimolar concentrations, and thereby are significantly more potent than the truncated Δtat mutant. Such transdominant mutants were constructed by substituting neutral amino acids at specific amino acid residues in the basic domain of Tat. The substitution Tat mutants are shown to inhibit tat gene expression to a much greater degree and at lower concentrations. For example, the substitution mutants inhibit tat gene expression at an equimolar or 3-fold excess over wild-type in vitro while truncated Δtat mutant inhibits wild-type expression only when present at a 10- to 20-fold excess, relative to wild-type, in vitro.

Most specifically, the present invention provides for a transdominant mutant HIV Tat protein which is capable of inhibiting HIV gene expression comprising a protein encoded by a particularly substituted mutant tat gene having a substituted basic domain. Examples of the specific nucleotide and protein sequences of the substituted mutant tat gene of the invention are provided at FIG. 7 (see FIG. 7), which depicts a tat mutant A (tat 52/57) (SEQ ID NO: 19 (nucleotide) and SEQ ID NO: 1 (protein)), a tat mutant B (tat 54/57) (SEQ ID NO: 21 (nucleotide) and SEQ ID NO: 3 (protein) and a tat mutant C (tat 55/58) (SEQ ID NO: 22 (nucleotide) and SEQ ID NO: 5 (protein).

The transdominant mutant HIV Tat proteins of the present invention may be further defined as a protein encoded by a substituted mutant tat gene having an amino sequence with an overall neutral or positive charge. In order to provide a protein with an overall neutral or positive charge, the amino acid sequence encoding the mutant Tat protein will include an amino acid substitution of a glycine and/or alanine amino acid at the basic domain region of the protein. The transdominant mutant HIV Tat protein may also take the form of a fusion protein.

Particular examples of the transdominant mutant HIV Tat protein include those proteins which are encoded by a tat 52/57 mutant (having a nucleotide sequence depicted in SEQ ID NO: 1), a tat 54/57 mutant (having a nucleotide sequence depicted in SEQ ID NO: 3) or a tat 55/58 mutant sequence (having a nucleotide sequence depicted in SEQ ID NO: 22). The designation "tat" is employed to define the tat gene which includes the nucleotide sequence of each of the mutants, while the designation "Tat" is used to designate the amino acid sequence of the mutant protein. Where the tat mutant is tat 52/57, the sequence of the mutant gene may be further defined as encoding the amino acid sequence Gly-Gly-Ala-Gly-Gly-Gly SEQ ID NO: 4 at amino acid positions 52–57 in the mutant Tat protein. Where the particular tat mutant is the herein described tat 54/57 mutant, the nucleotide sequence encoding said mutant protein may be further defined as encoding an amino acid sequence Ala-Gly-Gly-Gly SEQ ID NO: 6 at amino acids 54–57 of the mutant protein. Where the transdominant mutant HIV Tat protein is encoded by the tat 55/58 mutant, the tat mutant gene is further described as included a nucleotide sequence which encodes an amino acid sequence Gly-Ala-Gly-Gly SEQ ID NO: 7 at amino acids 55–58 of the mutant Tat protein.

However, substitutions of any of the amino acids between amino acids 52 and 58 which disrupt the basic change of the protein may provide a transdominant tat mutant having the capability of inhibiting HIV gene expression in the presence of an equimolar concentration of a wild type Tat protein.

The tat 52/57 mutant, tat 54/57 mutant and tat 55/58 mutant encode HIV Tat proteins which include 72 or less amino acids. These 3 particular mutant tat gene constructs are also referred to throughout the present specification as mutant A, mutant B, and mutant C, respectively.

The referenced mutant HIV Tat constructs are shown by the present inventors to be capable of inhibiting HIV gene expression in the presence of an equimolar concentration of a wild-type Tat protein in vitro. Slight variations of these mutant protein constructs are also expected to provide the same inhibition of HIV gene expression at equimolar concentrations, and are therefore considered to be within the spirit and scope of the present invention.

More generally speaking, the transdominant mutant HIV Tat protein(s) of the present invention may be described as being encoded by a transdominant mutant tat gene which includes four or six amino acid codon substitutions within the basic domain of the Tat protein. The basic domain of the tar gene is defined as encoding a mutant protein having a mutated amino acid sequence within the sequence which encodes amino acids 49–57 of the first 72 amino acids of the native Tat protein (see FIG. 1). It is at this basic domain where specific substitutions of amino acids having a neutral or negative charge are inserted to provide the potent, HIV Tat protein-inhibiting agents of the present invention.

In still another aspect of the present invention, specific truncated mutant HIV Tat proteins are provided which are also demonstrated to be capable of inhibiting HIV gene expression in the presence of an equimolar concentration of a wild type Tat protein in vitro. These particular truncated HIV Tat mutants may be further described as consisting essentially of less than the first 54 amino acids of the native Tat protein, or as consisting essentially of between 55 and 72 of the first 72 amino acids of the native Tat protein. In a most preferred embodiment, the transdominant mutant HIV Tat protein is defined as consisting essentially of 52 amino acids, wherein the 52 amino acids are the first 52 amino acids of the native Tat protein (see FIG. 1). Another most preferred embodiment of the truncated HIV mutant Tat proteins of the invention may be described as consisting essentially of 56 amino acids, again where the 56 amino acids consist essentially of the first 56 amino acids of the native Tat protein.

The particular transdominant mutant HIV Tat proteins may also within the scope of the present invention constitute proteins which are encoded by either or both a truncated or substituted basic domain tat gene mutant. For example, a truncated mutant of 57 amino acids in length may be prepared wherein the particular nucleotide substitutions defined herein for mutant tat B are included within the nucleotide sequence encoding a mutant Tat protein having a length of 57 amino acids. Similarly, a truncated and substituted Tat mutant of 57 amino acids may be prepared wherein the particular basic domain nucleotide substitution described for tat mutant A (52/57) is included within the nucleotide sequence. Ultimately, a truncated and substituted mutant Tat protein may be constructed which is encoded by a sequence of 58 amino acids, wherein a particular nucleotide substitution as defined for tat mutant C 55/58, is included within the nucleotide sequence encoding the mutant protein. Other permutations of the specific embodiments may also be envisioned, and would be expected to inhibit wild-type Tat function at equimolar concentrations in vitro, as well as in vivo.

The transdominant mutant HIV Tat proteins of the present invention may be even further described as constituting a substituted transdominant mutant tat gene as included within an expression vector. By way of example, such an expression vector may constitute any expression vector which contains an SV40 or cytomegalovirus promoter. For example, such an expression vector may be pDEX.

The mechanism of transdominant inhibition of wild-type Tat function has also been clarified in the present disclosure. Contrary to results reported in a previous work (*Proc. Natl. Acad. Sci.*, 87:5079–5083 (1991), it has been found that particular transdominant Tat mutants do not inhibit the ability of wild-type Tat to localize to the nucleus, indicating that it did not alter nuclear localization. Furthermore the particular transdominant Tat mutant 52/57 of the present invention was found to be able to inhibit the ability of R17-Tat fusions to activate gene expression from HIV-1 constructs containing R17 binding sites in place of TAR, thus indicating that intact TAR RNA is not required for inhibition. Attempts to demonstrate dimer formation between Tat and the transdominant mutant have proven unsuccessful. Thus, the most likely mechanism of transdominant Tat inhibition is the interaction with a cellular intermediate required for wild-type Tat function.

Though studies on the positive effects of Tat on HIV-1 gene expression have been useful in determining its function, studies concerning the inhibition of Tat function will be as, if not more, important in not only determining the effects of Tat on HIV gene expression, but in also formulating compounds and therapeutic agents for effectively controlling HIV-1 gene expression in vivo.

Therapeutic agents and methods of treatment for HIV-1 infections, including AIDS and ARC, are also within the scope of the present invention.

Most specifically, a therapeutic agent for the treatment of an HIV infection comprising a transdominant mutant HIV Tat protein capable of inhibiting HIV gene expression in the presence of an equimolar concentration of a wild type Tat protein in vitro is provided. As a therapeutic agent, the transdominant mutant HIV Tat protein is most preferably included within a pharmaceutically acceptable adjuvant. The particular mutant HIV Tat proteins of the therapeutic agents to be used in the treatment of HIV infection may be defined as a Tat protein comprising 72 amino acids or less. These 72 amino acids in preferred embodiments include at least one of the following amino acid sequences within the basic domain region of the protein: Gly-Gly-Ala-Gly-Gly-Gly SEQ ID NO: 4, Ala-Gly-Gly-Gly, SEQ ID NO: 6, or Gly-Ala-Gly-Gly SEQ ID NO: 7. Among these, the most common preferred amino acid sequence substitution to be included within the particular mutant Tat protein is the sequence Gly-Gly-Ala-Gly-Gly-Gly SEQ ID NO: 4. However, other amino acid substitutions may also be useful to create transdominant Tat proteins of the present invention.

Examples of the substituted mutant tat gene which encode the particular mutant Tat protein to be included within the herein described therapeutic agents may be further described as a tat 52/57, a tat 54/57 or a tat 55/58 gene mutant. The most preferred of these mutant tat genes which encode the mutant Tat proteins to be used in preparing the described therapeutic agent is the tat 52/57 gene mutant.

The therapeutic agents of the present invention may be further defined as comprising a fused bacterial-viral protein, a cellular ligand-viral protein or a viral epitope CD viral protein. These fusion proteins may be generally defined as bacterial or cellular fusions with the viral protein. More specifically, the tat protein may be fused to histidine residues (from 4 to 8) to aid in the purification of the transdominant tat protein from bacteria using nickel chromatograph (Gentz et al.). In addition, fusion of the transdominant Tat protein to a variety of ligands, such as IL-2 CD product in bacteria, can be considered to specifically target the fusion protein. The pharmaceutically acceptable adjuvant to be included with the transdominant mutant HIV Tat protein may comprise any adjuvant which is suitable for use in an animal, most particularly a human. By way of example, delivery may be in normal saline, albumin, or liposomes for intravenous administration.

The therapeutic agents of the present invention include a transdominant mutant HIV Tat protein which may be further defined as either a substituted transdominant mutant HIV Tat protein or a truncated transdominant mutant HIV Tat protein. In addition, it is contemplated that combinations of the herein described truncated transdominant mutant HIV Tat proteins and substituted transdominant mutant HIV Tat proteins may constitute still another embodiment of the present invention. The therapeutic agents of the present invention may also include substituted forms of the truncated transdominant Tat mutant proteins described herein. For example, a truncated mutant having 57 amino acids may include the particular amino acid sequence substitutions between amino acid residues 54–57, as described herein for Tat mutant B (54/57) or the substitutions between amino acids 52 to -57 as described for Tat mutant A (tat 52/57).

Turning now to a more specific description of the particular truncated transdominant Tat mutants of the present invention, therapeutic agents which include a transdominant Tat protein of 54 amino acids or less, referring to the first 54 amino acids of the Tat protein, may be employed as the therapeutic agent of choice, together in a pharmaceutically acceptable adjuvant. Particularly preferred truncated Tat mutant proteins which include less than 54 amino acids may be further defined as consisting essentially of 49, 50, 51, 52 or 53 amino acids. Therefore, the particular transdominant mutant tat gene would most preferably include sufficient amino acid codons directed to encoding these particular length proteins. Of the aforedescribed truncated transdominant mutant Tat proteins, one of the most preferred is a 50 amino acid length transdominant mutant Tat protein encoded by the corresponding appropriate transdominant mutant tat gene.

The therapeutic agent of the invention is to be formulated so as to be suitable for administration to an animal. By way of example, where the therapeutic agent constitutes the mutant Tat protein, the protein should be formulated so as to be suitable for administration by an intravenous route. Where the therapeutic agent constitutes the transdominant tat gene, it is contemplated that the therapeutic agent will take the form of a retroviral vector to include at least one of the mutant tat genes described herein, or an HIV vector which includes at least one of the mutant tat genes described herein.

Most preferably, the therapeutic agent as described as including either the mutant Tat protein or mutant tat gene will be formulated so as to be suitable for administration to a human.

In still another embodiment of the therapeutic agent, a mutant Tat truncated protein consisting essentially of 55, 56, 57 or 58 amino acids is provided. Such truncated Tat proteins are encoded by a corresponding truncated transdominant mutant tat gene. Again, the mutant Tat protein is formulated together in a pharmaceutically acceptable adjuvant. Of the described truncated mutant Tat proteins, a mutant Tat protein consisting essentially of 56 amino acids constitutes a preferred embodiment of the protein, and is encoded by a corresponding transdominant mutant tat gene.

In still another aspect of the present invention, a recombinant vector comprising a DNA sequence encoding the mutant Tat proteins herein described is provided. The various HIV vectors may also be employed in a method for producing the mutant Tat proteins. For example, the HIV vectors may be used to infect 293 cells which may in turn be cultured and the killed infected cells used as a source of vaccine. In this manner, both the method of delivery of the transdominant mutant, and the ability to produce the vector are unique. The DNA sequence may encode either the transdominant Tat substitution mutant proteins or the transdominant Tat truncated mutant proteins, or a combination thereof. In a most preferred embodiment, the recombinant vector comprises a nucleotide sequence of SEQ ID NO: 19, SEQ ID NO: 21, or SEQ ID NO: 22. The recombinant vector is to be constructed so as to be capable of replication within a host.

Retroviral vectors may also be used as a recombinant vector. In one aspect of the invention, the retroviral vectors are those which do not replicate. The retroviral vectors, in accordance with the present invention, will be used to produce stable cell lines which contain the transdominant tat gene mutant A, B or C nucleotide sequence. Specifically, the retroviral vector preferably is to include a nucleotide sequence as defined for SEQ ID NO: 19, SEQ ID NO: 21 or SEQ ID NO: 22. By way of example, human bone marrow cells can be infected with the aforedescribed retroviral vectors. These infected cells would thereby become resistant to HIV-1 gene expression.

One particular example of the HIV vector which the present inventors have constructed which delivered the transdominant tat gene mutant to cells was prepared by a unique method involving a pBR322 plasmid vector. A drug resistance gene, such as for puromycin or G418 resistance, is most preferably introduced into the HIV genome. These drug resistance genes provide protection against puromycin and G418. These resistance genes are most preferably inserted into the HIV genome at the nef open reading frame.

The above-described retroviral vectors, which by way of example include the pBRHIV-Δ NEF, pBRHIV-puro, and pBRHIV-neo vectors detailed herein in the examples, may then be used to infect permanent cell lines. By way of example, the present inventors have grown these HIV vector constructs on a cell line known as 293. 293 cells are CD4⁻ human embryonic kidney cells that express E1a and E1b proteins from adenovirus. Prior difficulties associated with this cell line of short lived low mutated viral production upon infection, and rapid and elimination from cell pools, were overcome using the inventors techniques of selecting for a purified population of cells which produce the herein described recombinant HIV. The infected cell lines of the present invention provide for the production of the mutant HIV virus, most particularly HIV virus which produce the mutant Tat protein, in large quantities. This technique is particularly novel in light of the above-described difficulties described in the art because it allows for both the production of mutant HIV virus in large quantities. Such may potentially be used, in killed form, as a vaccine. In addition, both the method of delivery of the transdominant mutant, and the technique used to produce the vector are unique.

In still another aspect of the present invention, a recombinant host bearing the recombinant vector described above is provided. The recombinant host will be prepared so as to be capable of expressing the mutant Tat protein of the present invention which is capable of inhibiting HIV gene expression. The transdominant mutant HIV Tat protein is again encoded by a substituted mutant tat gene which may be selected from those presented at FIG. 7. The recombinant host of the present invention will also be capable of expressing at least one of the mutant Tat proteins described herein. By way of example, the recombinant host may be further defined as a *Saccharomyces cerevisiae. E. coli Baculovirus* or a *Vaccinia* virus host.

In still another aspect of the present invention, a method of inhibiting HIV replication in an animal is provided. The method comprises treating the animal with a therapeutically effective amount of those therapeutic agents described herein. By way of example, such therapeutic agents include a transdominant Tat mutant protein formulated together with a pharmaceutically acceptable adjuvant. Again, the trans-dominant Tat mutant protein may constitute either truncated or substituted mutant Tat proteins, and, by way of example, may be those particular Tat mutant proteins encoded by the substituted tat mutant genes A (tat 52/57), B (tat 54/57) or C (tat 55/58).

In addition, the transdominant Tat mutant proteins may comprise those truncated mutants described herein, which, by way of example, include those proteins having less than 54 amino acids, most preferably between 49 and 53 amino acids, or having between 55 and 58 amino acids. Again, the reference number of amino acids in the protein, in regard to the truncated transdominant Tat mutant proteins refers to the first 58 amino acids of the native Tat protein. (See FIG. 1). Most preferably, the therapeutic agent should, be formulated so as to be suitable for administration to an animal intravenously. However intramuscular administration may be possible. It is contemplated that the therapeutically effective amount of the Tat mutant protein will vary depending upon the particular transdominant Tat mutant protein selected.

In a most preferred embodiment, the therapeutic agent is to be administered intravenously in the case of purified transdominant Tat proteins and also in the case of retroviral vectors or recombinant HIV vectors containing the transdominant tat gene mutant. In the case of these later viral vectors, it may be desirable to harvest patient cells, infect them in tissue culture and then infuse those cells into the patient. Such may provide a method of immunizing the patient to HIV. Most preferably, the methods and therapeutic agents employed in the present invention will be formulated so as to be suitable for the treatment of a human.

The inventors laboratory has been successful in constructing transdominant Tat mutants which antagonize the activity of wild type Tat. While transdominant mutants of other viral transactivator proteins, including the adenovirus E1A protein, the herpesvirus VP16 protein,[24] and the HTLV tax proteins have been constructed, never before have the specific transdominant mutants of the Tat protein been described. Transdominant mutants of viral transactivator proteins must usually be present in a several molar excess over the wild-type protein to suppress gene expression. Moreover, these mutants possess very defective activation phenotypes. In contrast, the presently described mutant Tat proteins are demonstrated to be effective in modulating gene expression at equimolar concentrations, making them superior viral gene suppressing agents to those previously available.

The following abbreviations are used throughout the description of the present invention:

AIDS—Acquired Immunodeficiency disease

CAT—CHLORAMPHENICOL ACETYLTRANSFERASE

HIV—human immunodeficiency virus

TAR—trans-activation response element

Tat—a viral regulatory protein

LTR—long terminal repeat

RSV—Rous sarcoma virus tat—a gene which encodes part or mutated forms of the Tat protein

BRIEF DESCRIPTION OF THE DRAWINGS

FIG. 1—Construction of Tat mutants. The first 72 amino acids SEQ ID NO: 2 of Tat and the first 219 nucelotides encoding Tat (SEQ ID NO: 20) are indicated. The position of stop codons introduced at amino acids 49, 50, 51, 52, 53, 54, 55, 56, 57, and 58 are indicated. The boxed regions (solid line, A [tat 52/57]; broken line, B [tat 54/57]; and hatched line, C [tat 57/58]) indicate amino acid substitutions with either glycine or alanine for each of the respective mutants.

FIG. 7(PANAS A–C)—FIG. 7A demonstrates the Tat mutant A (tat 52/57), which is also referred to as SEQ ID NO: 1 (amino acid) and 19 (nucleotide).

FIG. 7B demonstrates the Tat mutant B (tat 54/57), which is also referred to as SEQ ID NOS: 3 (amino acid) and 21 (nucleotide).

FIG. 7C demonstrates the Tat mutant C (tat 55/58), which is also referred to as SEQ ID NOS: 5 (amino acid) and 22 (nucleotide).

Figure 2A:
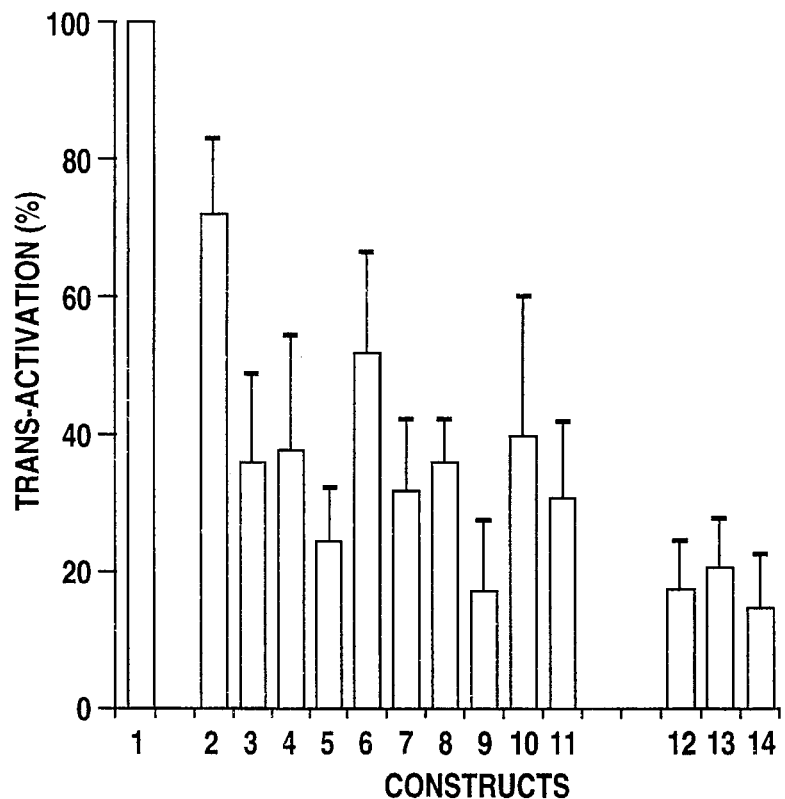
FIG. 2—Transdominant mutants inhibit trans-activation by Tat. (A) A vector (0.1 µg) expressing wild-type Tat alone (lane 1) or in the presence of equimolar concentrations of a vector expressing transdominant Tat mutants with truncations at amino acid 49 (lane 2), 50 (lane 3), 51 (lane 4), 52 (lane 5), 53 (lane 6), 54 (lane 7), 55 (lane 8), 56 (lane 9), 57 (lane 10), 58 (lane 11) or containing multiple amino acid substitutions, tat 55/58 (lane 12), tat 54/57 (lane 13), and tat 52/57 (lane 14), were transfected into HeLa cells with 5 µg of HIV-1 LTR CAT plasmid. The final concentration of the RSV constructs in each transfection was kept constant (5 µg) by the incorporation of RSV-β-globin. 100% conversion reflects the CAT activity obtained from the HIV-1 LTR CAT construct in the presence of wild-type Tat. The percentage of trans-activation for each Tat mutant was calculated relative to wild-type Tat. The results show the average of four independent experiments. (B) The same constructs were transfected as in (A), except that there was a 20-fold molar excess of the vector expressing a transdominant Tat mutant (2 µg) over the vector expressing wild-type Tat (0.1 µg).

The new mutants which may be used in conjunction with the present recombinant HIV vector, will be those described previously (Malim et al. (1989) Cell, 58:205–214).

DETAILED DESCRIPTION OF THE PREFERRED EMBODIMENTS

The present inventors have constructed expression vectors used by David Eisenberg's laboratory (Molecular Biology Institute, UCLA 405 Hilgard Avenue, Los Angeles, Calif. 90024) to purify and crystallize Tat.

The effectiveness of a transdominant Tat mutant is dependent on two criteria. One is defective activation of HIV LTR gene expression and the other is the ability to antagonize wild-type Tat function. The present disclosure also outlines methods by which additional transdominant Tat mutants may be constructed and used to generate mutants which satisfy these criteria and serve as better transdominant mutants.

The amino acid sequence of the first 72 amino acids of the Tat protein and the first 219 nucleotide encoding the Tat protein (SEQ ID NO: 20) are illustrated in Table 1 SEQ ID NO: 2.

TABLE 1

| | | | | | | Amino-Terminal Domain | | | | | | | | | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |
| MET | Glu | Pro | Val | Asp | Pro | Asn | Leu | Glu | Pro | Trp | Lys | His | Pro | Gly | Ser |
| ATG | GAG | CCA | GTA | GAT | CCT | AAT | CTA | GAG | CCC | TGG | AAG | CAT | CCA | GGA | AGT |
| | | | | | | | | | | | | Cysteine-Rich Domain | | | |
| 17 | 18 | 19 | 20 | 21 | 22 | 23 | 24 | 25 | 26 | 27 | 28 | 29 | 30 | 31 | 32 |
| Gln | Pro | Arg | Thr | Ala | Cys | Asn | Asn | Cys | Tyr | Cys | Lys | Lys | Cys | Cys | Phe |
| CAG | CCT | AGG | ACT | GCT | TGT | AAC | AAT | TGC | TAT | TGT | AAA | AAG | TGT | TGC | TTT |
| 33 | 34 | 35 | 36 | 37 | 38 | 39 | 40 | 41 | 42 | 43 | 44 | 45 | 46 | 47 | 48 |
| His | Cys | Tyr | Ala | Cys | Phe | Thr | Arg | Lys | Gly | Leu | Gly | Ile | Ser | Tyr | Gly |
| CAT | TGC | TAC | GCG | TGT | TTC | ACA | AGA | AAA | GGC | TTA | GGC | ATC | TCC | TAT | GGC |
| | | | Basic Domain | | | | | | | | | | | | |
| 49 | 50 | 51 | 52 | 53 | 54 | 55 | 56 | 57 | 58 | 59 | 60 | 61 | 62 | 63 | 64 |
| Arg | Lys | Lys | Arg | Arg | Gln | Arg | Arg | Arg | Ala | Pro | Gln | Asp | Ser | Gln | Thr |
| AGG | AAG | AAG | CGG | AGA | CAG | CGA | CGA | AGA | GCT | CCT | CAG | GAC | AGT | CAG | ACT |
| 65 | 66 | 67 | 68 | 69 | 70 | 71 | 72 | | | | | | | | |
| His | Gln | Ala | Ser | Leu | Ser | Lys | Gln | | | | | | | | |
| CAT | CAA | GCT | TCT | CTA | TCA | AAG | CAG | TAA | | | | | | | |

Changes in the basic region of Tat protein and the tat gene are illustrated in Table 1 appear essential to generate transdominant Tat mutants. A number of neutral amino acid substitutions in the basic domain of Tat between amino acids 49 and 57 result in transdominant Tat mutants. According to the present invention, this basic region was further mutated by substituting neutral amino acids in various novel combinations between amino acids 49 and 57 of the tat gene. A variety of mutants will also be constructed which substitute glutamic acid, rather than the neutral amino acids glycine or alanine, for basic region amino acids. Each construct was assayed in cotransfection assays with HIV LTR CAT and wild-type tat plasmids to better determine the role of amino acid charge on the generation of transdominant Tat mutants. Previous mutagenesis studies have been analyzed by the present inventors, and indicate that preservation of at least three basic amino acids at positions 49, 50, and 51 of the tat gene are critical for the transdominant tat phenotype.

Indirect Immunofluorescence

HeLa cells were grown on 100-mm tissue culture plates in Iscoves' medium supplemented with 5% newborn calf serum. At 70 to 80% confluency, the cells were trypsinized and washed twice with 25 to 30 volumes of media. The cells were centrifuged at 1500 rpm for 5 min, the pellet was resuspended in a proper volume of medium to reach about $10^7$ cells per milliliter. Cells ($2\times10^6$) were electroporated in the presence of 20 μg of plasmid with a BRL electroporator (at a capacitance of 1180 μF, low resistance, and 250 V). The electroporated cells were resuspended with 1 ml of medium and plated on gelatin-covered glass coverslips.

Cells on coverslips were rinsed with phosphate-buffered saline (PBS) and fixed with methanol at −20° C. for 5 min. After the cells were washed with PBS, they were placed in 50 mM Tris (pH 7.4), 150 mM NaCl, 5% normal goat serum (PBS-NGS), and 0.02% azide for at least 45 min. For indirect immunofluorescence, the samples were incubated with the primary antibody, which was a rabbit polyclonal antibody to a peptide corresponding to amino acids 1 to 17 of the Tat protein as described by Pearson et al., 1990, or a mouse monoclonal antibody directed against the basic domain of Tat as described by Brake et al., 1990, which references are both specifically incorporated herein by reference for this purpose, or both antibodies in the case of double staining. Incubation with the antibodies, diluted 1:400 with PBS-NGS, was at room temperature for 1 h. After washing three times with PBS-NGS, a 1:100 dilution of secondary antibody solution consisting of fluorescein-conjugated goat antiserum to mouse IgG or rhodamine-conjugated goat antisense to rabbit IgG was added to the samples, which were incubated for 1 h. After further washes, the coverslips were mounted on slides in Fluormount G mounting medium. Cells were visualized with a 63× Planapo lens on a light fluorescence microscope.

Even though the present invention has been described with a certain degree of particularity, it is evident that many alternatives, modifications, and variations will be apparent to those skilled in the art in light of the following disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

CONSTRUCTION OF TRUNCATED AND SUBSTITUTED Tat MUTANTS

To further characterize the requirements for transdominant inhibition by Tat, a series of mutant Tat proteins are described herein which were prepared by (i) introducing stop codons at different positions in the gene that would alter the basic domain of the protein, or (ii) substituting multiple neutral amino acid codons for basic amino acid codons.

Two types of mutations were used to construct the variety of proteins of the present invention having an altered basic domain (FIG. 1). In one type, stop codons that altered the basic domain of Tat between amino acids 49 and 58 were introduced and resulted in a variety of truncated Tat constructs. In the other type of mutations, we substituted different basic domain codons (A [tat 52/57], B[tat 54/57], and C[tat 55/58]) with codons for neutral amino acids thus changing the overall basic charge of the Tat protein (FIG. 1).

The fragment HincII-SspI corresponding to the second exon of tat was cloned into the HincII site of pUC19. For oligonucleotide-directed mutagenesis a HindIII-BamHI fragment was cloned into M13mp18 as previously described (Garcia et al., 1988). The oligonucleotides made to the coding strand of tat contained the mutations shown in FIG. 1. For substituted constructs, the A (tat 52/57) mutant containing Gly-Gly-Ala-Gly-Gly-Gly SEQ ID NO: 4 in place of Arg-Arg-Gln-Arg-Arg-Arg SEQ ID NO: 8 was prepared with the use of an oligonucleotide with the sequence 5'-GGG GGA GCC GGC GGA GGA-3; SEQ ID NO: 9 the B (tat 54/57) mutant containing Ala-Gly-Gly-Gly SEQ ID NO: 6 in place of Gln-Arg-Arg-Arg SEQ ID NO: 10 was prepared with the use of an oligonucleotide with the sequence 5'-GCC GGC GGA GGA-3' SEQ ID NO: 11; and the C (tat 55/58) mutant containing Gly-Ala-Gly-Gly SEQ ID NO: 7 in place of Arg-Arg-Arg-Ala SEQ ID NO: 12 was prepared with the use of an oligonucleotide with the sequence 5'-GGA GCC GGC GGT-3'SEQ ID NOS: 13. The synthesized oligonucleotides were treated with polynucleotide kinase in the presence of ATP and used for mutagenesis according to the conditions described by the manufacturer of a commercial site-directed mutagenesis kit (Amersham) which reference is specifically incorporated herein by reference.

In the case of the truncated constructs, three stop codons (TGA TAA TAA) were added in frame, followed by a BglII site. DH5αF' cells were transformed with the mutagenized plasmids, positive plaques were determined by screening, and the sequences were confirmed by the dideoxy sequencing method.[reference?] Fragments containing the mutated tat genes were cloned into a eukaryotic expression vector, pDEX (Garcia et al., 1988).

These resulted in 3 substitution as well as truncated tat constructs. Each of these mutated tat constructs was cloned downstream of the RSV promoter in order to express the genes in transfection experiments.

EXAMPLE 2

BASIC DOMAIN MUTATIONS AND PRODUCTION OF TRANSDOMINANT TAT MUTANT PROTEINS

The present example is provided to demonstrate the utility of particular tat mutants for providing the synthesis of transdominant Tat mutant proteins and thereby demonstrate the in vivo utility of the claimed invention for inhibiting HIV expression and infection in vivo.

To demonstrate the effects of basic domain mutations on the ability of the mutant proteins to antagonize wild-type Tat activation, cotransfection experiments were performed.
Cell Transfection and CAT assays HeLa cells were maintained on complete Iscoves' medium supplemented with 5% newborn calf serum, 2.5% fetal bovine serum, and penicillin and streptomycin. At 24 h prior to transfection, the cell cultures were split and plated on 60-mm plates at a density that permitted them to reach between 50 and 70% confluency at the time of the transfection. The transfections were performed by the calcium phosphate technique in the presence of 5 μg of the HIV-1 LTR CAT construct and the amounts of RSV-Tat and the RSV-tat mutants indicated in each experiment. The total concentration of the RSV expression vector in each transfection was kept constant (5 μg) by the addition of an RSV-β-globin construct. At 4 h after transfection, the cells were subjected to a glycerol shock, and 48 h later they were harvested, washed, and resuspended in 100 μl of 0.25M Tris, pH 7.8. The cell extracts were prepared and CAT assays were done as previously described (Gorman et al., 1982). CAT activity from the HIV-1 LTR CAT construct was determined by measuring both unacetylated and acetylated $^{14}$C-labeled chloramphenicol. The specific level of HIV-1 LTR CAT trans-activation of each tat construct was determined by subtracting the basal level obtained with the RSV-β-globin construct alone. Using the specific levels of transactivation, the percent conversion of each tat construct was calculated relative to the trans-activation seen with wild-type Tat.

Figure 2B:
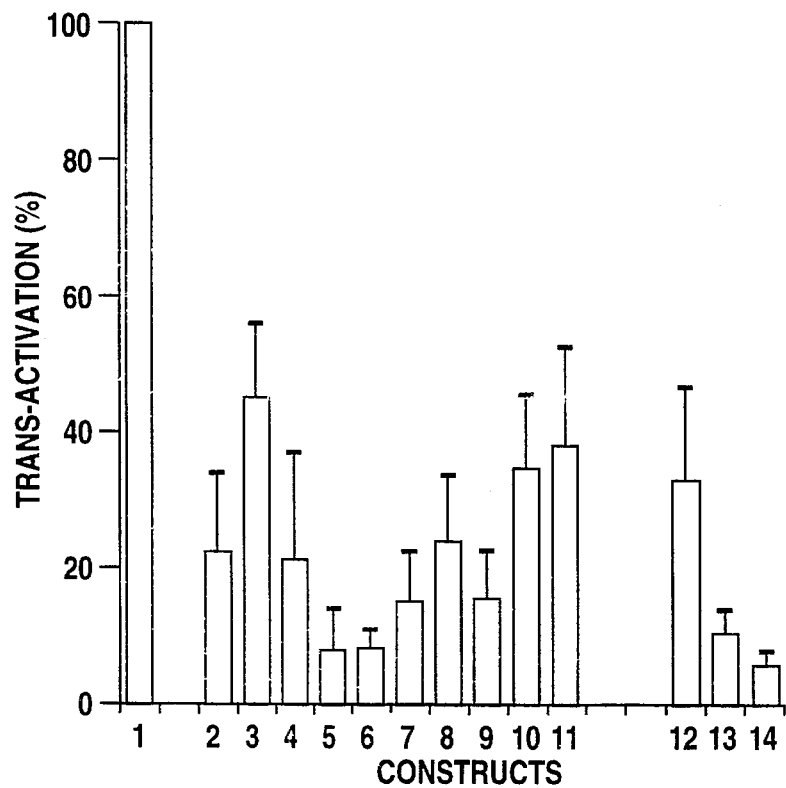

The HIV-1 LTR CAT plasmid was transfected with an RSV expression construct (Garcia et al., 1989) containing a mutated tat gene and a similar construct containing a wild-type tat gene in equimolar concentrations (FIG. 2A) or a 20-fold molar excess of the mutated tat construct over the wild-type tat construct (FIG. 2B). Transfected cells were harvested at 48 h and the level of trans-activation by Tat proteins was calculated by measuring CAT activity. The basal level of expression and the percentage of trans-activation were determined as described supra.

As shown in FIG. 2A, a number of truncations of the tat gene between the codons for amino acids 49 and 58 resulted in proteins that inhibited Tat activation when the vector expressing the mutant protein was transfected at equimolar concentrations with a vector expressing wild-type Tat (FIG. 2A, lanes 2 to 11). For most of these mutants, the degree of inhibition was 3- to 4-fold compared to the wild-type protein (FIG. 2A). However, equimolar concentrations of vectors expressing wild-type Tat and constructs A (tat 52/57), B (tat 54/57), and C (tat 55/58) (the substitution mutants) resulted in a 5- to 7-fold inhibition of wild-type Tat activation (FIG. 2A, lanes 12 to 14). Thus, proteins with the specific truncations or substitutions in the basic domain described above were able to inhibit Tat activation when their expression vectors were present in equimolar concentrations with a vector expressing wild-type Tat. This is in contrast to the inventors previously described Δtat mutant, which exhibited its maximal phenotype only when the vector expressing it was present in an 5- to 30-fold molar excess over a vector expressing the wild-type Tat.

When the concentration of each of the vectors expressing Tat proteins with truncations in the basic domain was increased to a 20-fold molar excess over the vector expressing the wild-type protein, further inhibition of wild-type Tat activation of the HIV-1 LTR was seen (FIG. 2B, lanes 2 to 11). Maximum inhibition occurred with constructs derived by introducing stop codons at positions 52, 53, and 54. (FIG. 2B, lanes 5 to 7). These constructs resulted in a 10- to 15-fold inhibition of wild-type Tat trans-activation of the HIV-1 LTR (FIG. 2B).

The substitution mutants, which include substitutions in the basic domain, also resulted in marked inhibition in Tat activation at these same molar excesses (FIG. 2B, lanes 12 to 14). This inhibition was most evident with a protein that had a substitution of six amino acids in the basic domain, C (tat 52/57) (FIG. 2B, lane 14). This mutant routinely resulted in a 15- to 20-fold inhibition of wild-type Tat activation when the vector expressing it was present in at least a 5-fold molar excess over the vector expressing the wild-type Tat.

These results indicated that both truncations and substitutions that alter the basic domain of Tat result in proteins that antagonize wild-type Tat activation of the HIV-1 LTR. However, the potency of each of the various mutant constructs is demonstrated to vary, depending on the particular substitution examined.

EXAMPLE 3

TRANS-ACTIVATION OF THE HIV-1 LTR BY TAT PROTEINS WITH AN ALTERED BASIC DOMAIN

To determine if the degree of inhibition correlates with residual trans-activation capability of the transdominant Tat mutants, each of the transdominant Tat mutants was tested for its ability to trans-activate the HIV-1 LTR (FIG. 3, A and B). The HIV-1 LTR CAT construct was cotransfected with the wild-type tat vector or each of the vectors expressing a transdominant Tat mutant. As in Example 1, the total concentration of the RSV expression vector in each transfection was kept constant by the addition of an RSV-β-globin vector.

Figure 3A:
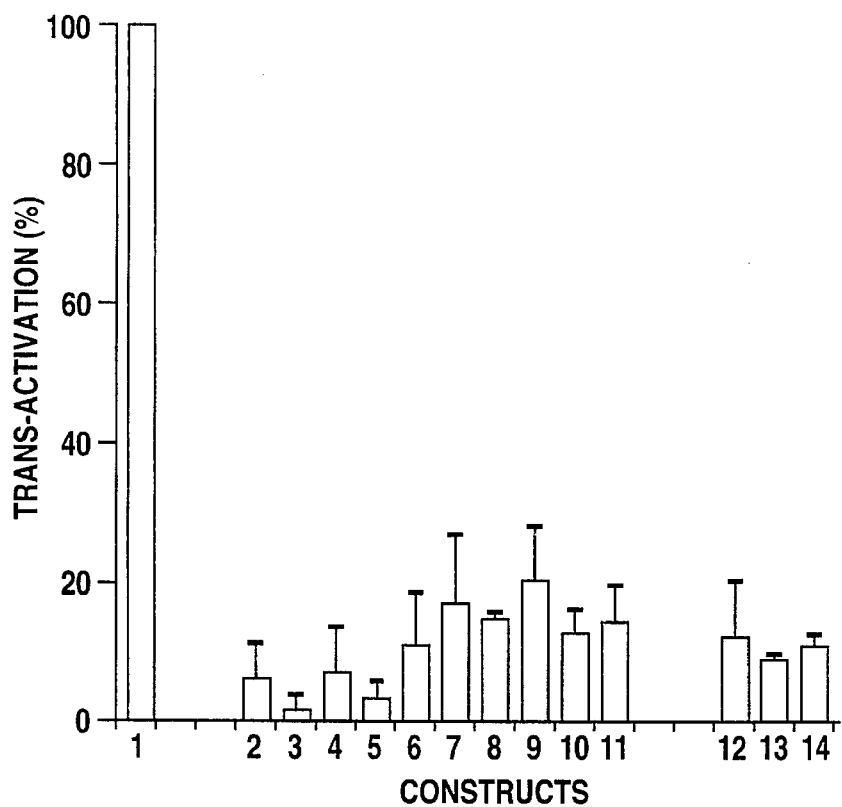
FIG. 3—Trans-activation by transdominant Tat mutants. (A) A vector (0.1 µg) expressing Tat alone (lane 1), or a vector (0.1 µg) expressing the transdominant mutants alone, including mutants with truncations at amino acid 49 (lane 2), 50 (lane 3), 51 (lane 4), 52 (lane 5), 53 (lane 6), 54 (lane 7), 55 (lane 8), 56 (lane 9), 57 (lane 10), 58 (lane 11) or with substitutions, tat 55/58 (lane 12), tat 54/57 (lane 13), and tat 52/57 (lane 14), were transfected into HeLa cells with 5 µg of HIV-1 LTR CAT construct. The final concentration of the RSV promoter in each transfection was kept constant (5 µg). 100% conversion reflects the CAT activity obtained from HIV-1 LTR CAT construct in the presence of wild-type Tat. The percentage of trans-activation for each Tat mutant was calculated relative to wild-type Tat. The results shows the average of four independent experiments. (B) The same constructs were transfected as in (A) only using 2.0 µg of each tat construct.

As shown in FIG. 3A, cotransfections of vectors expressing a mutant tat (0.1 μg) and HIV-1 LTR CAT constructs revealed that each of the proteins with an altered basic domain was defective in its ability to activate the HIV-1 LTR (FIG. 3A, lanes 2 to 14) compared to similar concentrations of a vector expressing wild-type Tat (FIG. 3A, lane 1). The maximum activation of the HIV-1 LTR with the mutant proteins was only 20% of that seen with wild-type Tat.

Figure 3B:
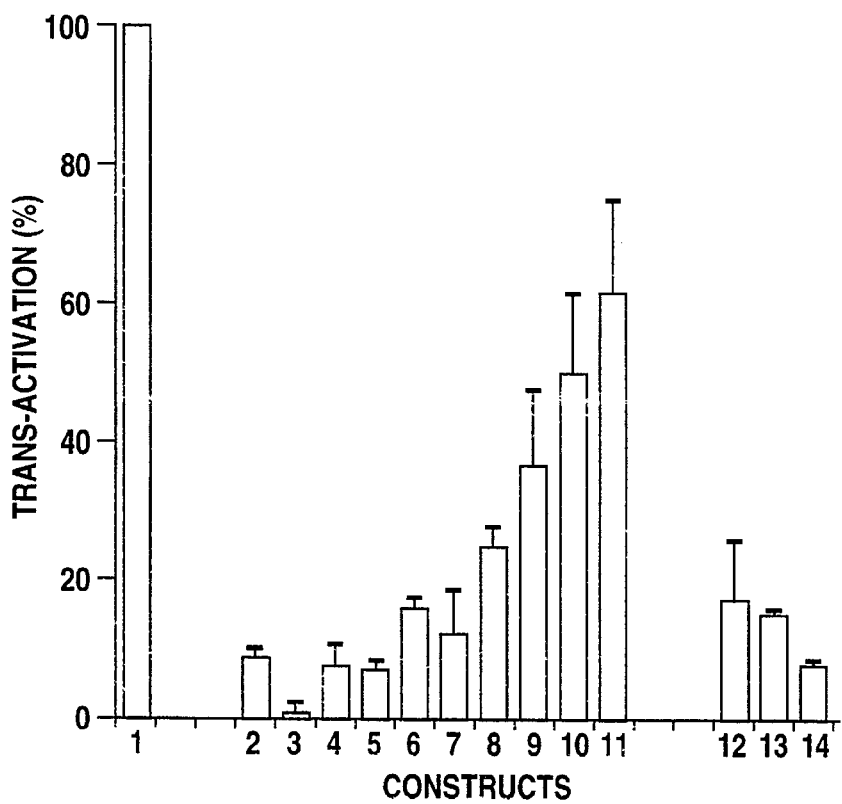

When the concentration of vectors expressing mutant Tat proteins was increased 20-fold (2.0 μg), mutants with truncations of the basic domain downstream of amino acid 55 reduced the level of activation of the HIV-1 LTR to 40 to 60% of that obtained with similar concentrations of the vector expressing wild-type Tat (FIG. 3B, lanes 8 to 11). However, at these same DNA concentrations, constructs containing multiple substitutions in the Tat basic domain were still severely defective in their ability to activate the HIV-1 LTR (FIG. 3B, lanes 12 to 14).

These results indicated that at low vector concentrations, proteins with an altered (substituted) basic domain were very defective in their ability to activate the HIV-1 LTR, while at higher vector concentrations, proteins with truncations between amino acids 55 to 58 were able to produce nearly wild-type levels of activation.

EXAMPLE 4

EFFECT OF TAR ELEMENT MUTATIONS ON TRANSDOMINANT INHIBITION

The present example is provided to demonstrate that mutations in the TAR RNA stem structure, the sequence of the bulge region, and the primary sequence of the loop of the TAR RNA structure influence to varying amounts the degree of transdominant inhibition with the tat 52/57 construct.

Figure 4A:
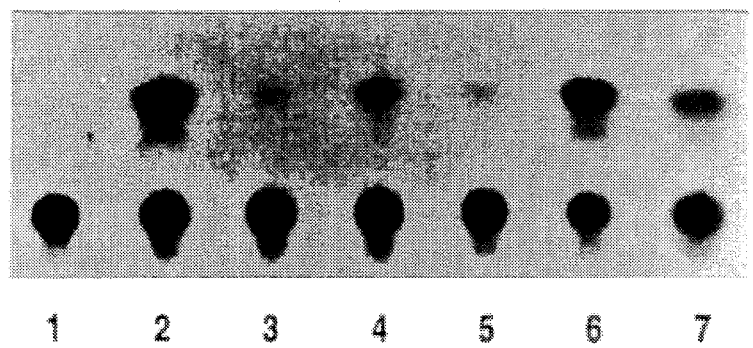
FIG. 4. Transdominant inhibition of TAR mutant constructs. (A) The wild-type HIV-1 LTR CAT plasmid was transfected into HeLa cells in the absence (lane 1) or presence of a vector expressing Tat (lane 2). In addition, the HIV-1 LTR CAT constructs containing mutations in the TAR loop (+31/+34) (lane 3), stem (+19/+22) (lane 4), stem (+40/+43) (lane 5) stem restoration (+19/+22)/(+40/+43) (lane 6), or a bulge mutation (+23) (lane 7) in the presence of a vector expressing wild-type Tat were transfected into HeLa cells and CAT activity was determined. (B) The same constructs as in (A) were transfected with a 5-fold excess of the tat 52/57 construct over wild-type tat.
Figure 4B:
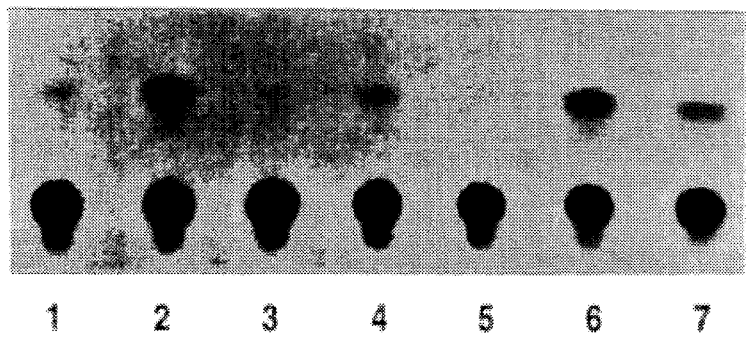

CAT activity produced by HIV-1 LTR constructs containing either wild-type TAR, or a variety of TAR mutants in the presence of a vector expressing wild-type Tat alone (FIG. 4A), or both wild-type Tat and tat 52/57 (FIG. 4B), were assayed as described herein. As shown in FIG. 4A, compared to wild-type TAR, mutations of the loop, stem, or bulge of TAR resulted in a marked decrease in wild-type Tat activation (FIG. 4A, lanes 2 to 7). By including tat 52/57 in these transfections in a 5-fold molar excess over the vector expressing wild-type Tat, the level of CAT activity produced with both wild-type and mutant TAR constructs was reduced approximately 5- to 10-fold (FIG. 4B, lanes 2 to 7).

These results demonstrate that transdominant inhibition by the substitution mutant tat 52/57, was not dependent on any single element of the TAR RNA structure, but was due to a general mechanism of Tat function.

EXAMPLE 5

TRANSDOMINANT ACTIVATION AND THE EFFECT OF NATIVE TAR ELEMENT

The lack of dependence of transdominant inhibition on the structure of the TAR RNA was confirmed and extended in the present example with tat 52/57 mutant effect on Tat-R17 fusion proteins.

Figure 5A:
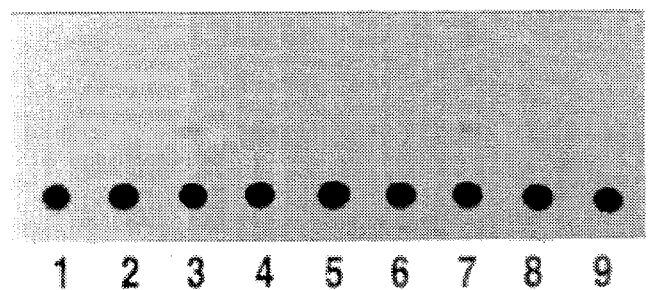
FIG. 5. Transdominant inhibition of Tat-R17 fusion proteins. (A) An HIV-1 construct containing an R17 recognition element in place of the TAR element was cotransfected with an expression vector containing the R17 gene (lane 1), the wild-type tat gene (lane 2), the Tat-R17 fusion protein alone (lane 3), tat 52/57 alone (lane 4) or with either an equimolar (lane 5) or 5-fold molar excess of tat 52/57 alone (lane 6), the Tat-R17 fusion protein with a deletion of amino acids 49/57 in the basic domain (lane 7), or this construct with either an equimolar (lane 8) or 5-fold excess of tat 52/57 (lane 9). (B) An HIV-1 -LTR CAT construct was transfected in the absence (lane 1) or presence of a vector expressing wild-type Tat (lane 2), with the Tat-R17 fusion protein alone (lane 3) or this construct in the presence of an equimolar (lane 4) or 5-fold excess of tat 52/57 (lane 5). DNA concentrations were adjusted as described in Materials and Methods.
Figure 5B:
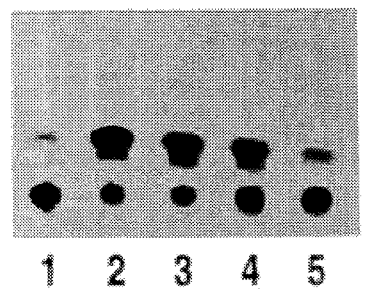

Both the tat-R17 construct (FIG. 5A, lane 3) and the tat-R17 construct with the basic domain deletion (FIG. 5A, lane 7) were able to activate the HIV-1 LTR that contained the R17 recognition element inserted into the TAR element to about 5% of the level of activation obtained with the wild-type HIV-1 LTR (FIG. 5B, lane 3). A previous report indicates that Tat-R17 fusion proteins were capable of activating the HIV-1 LTR containing R17 binding sites (Selby et al., 1990).

It was next determined whether either an equimolar or a 5-fold molar excess of tat 52/57 could inhibit HIV-1 LTR activation by tat-R17 constructs.

As demonstrated in FIG. 5, tat 52/57 was able to severely inhibit activation of R17 recognition element by both the Tat-R17 fusion protein (FIG. 5A, lanes 5 and 6) and the Tat-R17 protein with the basic domain deletion (FIG. 5A, lanes 8 and 9). CAT activity was inhibited by at least 10-fold compared to the activity measured in the absence of tat 52/57. Thus, the presence of an intact TAR element was not critical for transdominant inhibition. Furthermore, transdominant inhibition could occur in the absence of the wild-type Tat basic domain in Tat-R17 fusion proteins.

EXAMPLE 6

EFFECT OF TRANSDOMINANT Tat MUTANTS ON Tat NUCLEAR LOCALIZATION

It was important to study the mechanism by which transdominant mutants inhibited activation of the HIV-1 LTR by Tat. One potential mechanism of this inhibition was a defect in the nuclear localization of Tat in the presence of a transdominant Tat mutant (Pearson et al., 1990). The present example demonstrates co-transfection of a vector expressing wild-type Tat and a vector expressing a transdominant Tat mutant do not inhibit the nuclear localization of wild-type Tat.

To perform these studies, two types of antibodies were used. One was a rabbit polyclonal antibody to an amino-terminal Tat peptide corresponding to amino acids 1 to 17 of the Tat protein (Pearson et al., 1990) which was capable of recognizing both wild-type Tat and transdominant Tat mutant protein. The other was a mouse monoclonal antibody directed against a portion of the basic domain of Tat (Brake et al., 1990); this antibody reacts with wild-type Tat but not tat 52/57. A construct expressing wild-type Tat and an excess of a construct expressing a transdominant Tat mutant were transfected into HeLa cells. The cells were examined by immunofluorescence with the two antibodies, each one labeled with either rhodamine or FITC. The site of localization of both Tat and the transdominant mutant in the cotransfection assays could then be determined.

Figure 6A:
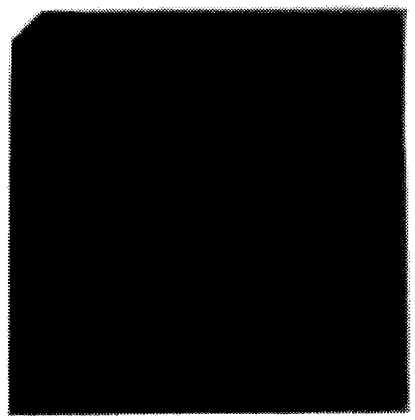
FIG. 6. Examination of the cellular localization of wild-type Tat and transdominant Tat mutants by indirect immunofluorescence. HeLa cells were fixed and stained as indicated in the description of the preferred embodiments. (A) Cells were transfected with a vector expressing wild-type Tat. Panel 1: Localization of the Tat protein was detected by indirect immunofluorescence staining with the use of a mouse monoclonal antibody to the basic domain of Tat (Brake et al., 1991) as the primary antibody and a rhodamine-conjugated goat antibody to mouse IgG as a second antibody. Panel 2: Examination of the same field by phase-contrast microscopy. (B) Cells were transfected with a vector expressing the tat 52/57 protein. Indirect immunofluorescence staining was used to detect the protein, with a rabbit polyclonal antibody to amino acids 1 to 17 of the Tat protein (Pearson et al., 1990) being used as the primary antibody and fluorescein-conjugated goat antibody to rabbit IgG as the secondary antibody. Panel 2: Examination of the same field by phase-contrast microscopy. (C) Cells were transfected with a vector expressing wild-type Tat and with a 5-fold molar excess of the vector expressing tat 52/57 protein. Localization of the Tat proteins was detected by double-indirect immunofluorescence staining, with the monoclonal antibody that reacts with wild-type Tat followed by rhodamine-conjugated goat antibody to mouse IgG (panel 1), and with the polyclonal antibodies that react with both wild-type Tat and tat 52/57, followed by the fluorescein-conjugated goat antibody to rabbit IgG (panel 2). Panel 3 shows the same field examined by phase contrast microscopy.
Figure 6B:
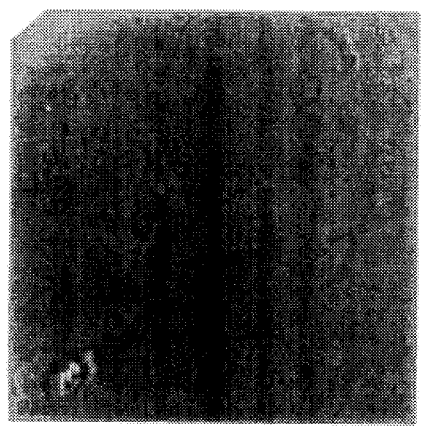
Figure 6C:
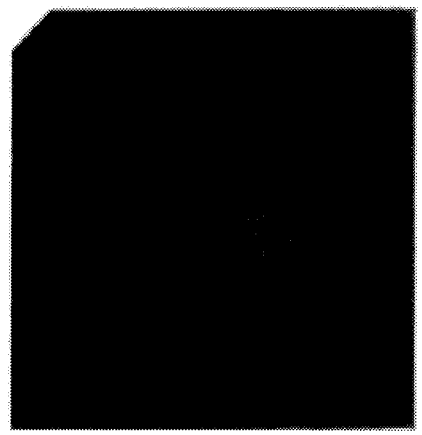
Figure 6D:
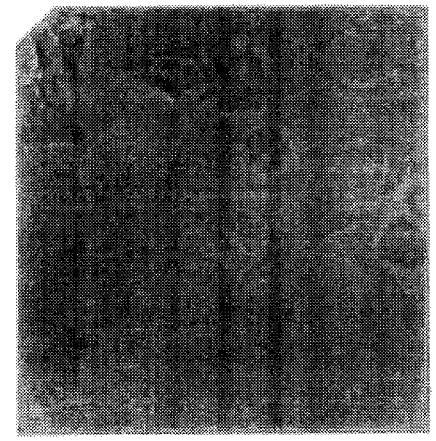
Figure 6E:
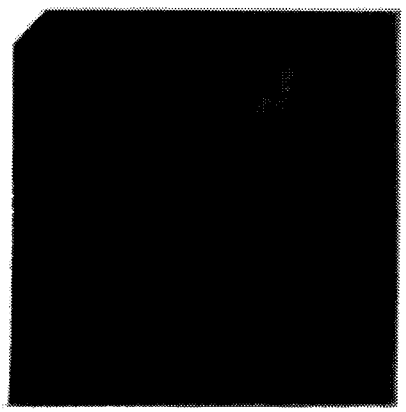
Figure 6F:
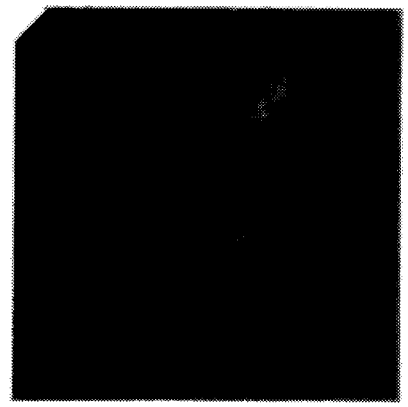
Figure 6G:
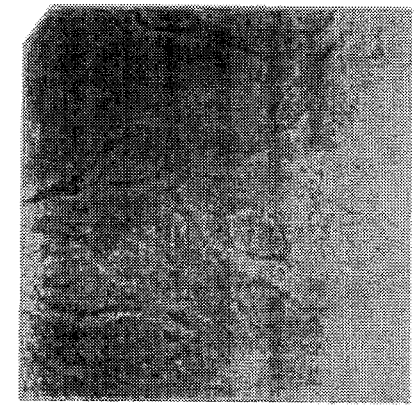

As shown in FIG. 6A, lane 1, Tat was localized primarily in the nucleus when the wild-type construct was transfected alone into HeLa cells (Hauber et al., 1987; Ruben et al., 1989; Hauber et al., 1989; Siomi et al., 1990;). When the tat 52/57 construct was transfected alone, tat 52/57 was present in both the nucleus and the cytoplasm (FIG. 6B). When the tat 52/57 vector was present in cotransfections in a 5-fold molar excess over the vector expressing wild-type Tat, the transdominant mutant protein was present in both the nucleus and the cytoplasm (FIG. 6B, lane 2) and wild-type Tat was present only in the nucleus (FIG. 6C, lane 1).

These results demonstrate that the transdominant mutant did not inhibit Tat function by significantly impairing its transport to the nucleus.

EXAMPLE 7

CONSTRUCTION OF ADDITIONAL TRANSDOMINANT Tat MUTANTS

Both PCR and M13 mutagenesis will be used to engineer additional mutations into the previously characterized tat transdominant mutant, Δtat, in which a stop codon was introduced at amino acid 54 (Pearson et al. (1990)). To construct mutations in the amino terminus of Δtat, PCR mutagenesis will be used to progressively delete from 2 to 18 amino acids.

To ensure that these truncated proteins are able to be expressed to high levels, a consensus Kozak's sequence will be inserted into the amino terminal oligonucleotide used for PCR. Deletion mutants will be created using M13 mutagenesis in the region of Δtat between amino acids 36 and 49. All mutants will be subject to DNA sequence analysis and assayed in cotransfection assays with the wild-type tat gene and a HIV-1 LTR CAT reporter plasmid to determine if these mutants still possess a transdominant phenotype. If transdominant Tat mutants containing fewer amino acids can be constructed, they would facilitate the synthesis of transdominant Tat peptides for cellular uptake by HIV-1 infected cells.

EXAMPLE 8

CONSTRUCTION OF CELL LINES CONTAINING TRANSDOMINANT Tat MUTANTS

The present example is provided to demonstrate a preferred method for preparing cell lines which contain transdominant Tat mutants, and to demonstrate the utility of the present invention for creating a transdominant Tat mutant cell line from virtually any cell line. Cell lines containing transdominant tat mutants are also described at Example 11.

Previous studies with a herpesvirus transdominant mutant in the transactivator protein VP16 revealed that this gene can be used to create stable cell lines which are resistant to infection by herpesvirus. The present inventors will use similar approaches to develop cell lines which are resistant to HIV-1 infection. Either the transdominant tat mutant, tat 52-57 (which substitutes glycine or alanine residues between amino acids 52 and 57 of Tat), or another tat mutant Δcys (which charges three critical cysteine residues at amino acids 22, 27, and 34 of the tat gene), was introduced into one of two Moloney virus derived retroviral vectors both of which contain neomycin resistance genes.[62] However, any of the transdominant tat mutants as described in the present disclosure may be inserted to provide cell lines with those particular corresponding transdominant Tat mutants.

One vector will use the Moloney LTR to direct expression of the tat genes. In the other vector, a metallothionein promoter inserted downstream of the Moloney LTR will direct synthesis of the tat cDNA. These retroviral vectors have been used to successfully express the transforming growth factor, b1.

Following insertion of the tat gene into these vectors, each vector will be transfected into the ecotropic-vector cell line, Y2, and cell lines selected with G418 as described. Ecotropic vector stocks will be used to infect PA317 cells, and following G418 selection, amphotropic stocks will be harvested and titers determined (Morganstern, J. P. and Land, H. (1990) *Nucl. Acids Res.*, 18:3587–3596). These stocks can be used to infect a variety of T-cells and monocyte cell lines. Each of these viruses will be used to infect a variety of T-lymphocyte cell lines including Jurkat and H9 and the monocyte cell line U937. Following selection with G418, resistant cell lines will be isolated and the presence of the transdominant tat gene confirmed by PCR analysis of DNA isolated from these cells and Western blot analysis using polyclonal Tat antibodies. These cells will then be tested for their ability to be infected with HIV-1 . Cell free supernatant containing HIV-1 will be used to infect cells and p24 Ag and reverse transcriptase levels will be performed daily as described. The metallothionein promoter within the retroviral vector is expected to be useful in production of the Tat protein.

The present inventors have found that production of high levels of the Tat proteins in stable lymphoid cell lines frequently proves toxic. Thus, the ability to induce tat with cadmium sulfate (1 mM) may make it possible to better propagate the cells and induce Tat production at the time of HIV-1 infection. This level of cadmium appears to be free of significant cellular toxicity, but control cell lines will be included in each experiment. Thus, the determination of whether either constitutive or inducible expression of transdominant tat mutants in stable cell lines alters their ability to be infected by HIV-1 may be made.

Transdominant tat mutants will also be introduced into HIV proviral constructs in place of the wild-type tat gene. Since the tat gene is critical for HIV-1 gene expression, very little viral expression would be expected in virus containing mutant tat genes, and it would likely prove difficult to obtain high titer stocks of such a virus. However, the advantages of using such a virus as a vector to deliver transdominant tat mutants to cells would be its low endogenous expression in uninfected cells and its potential inducibility by wild-type Tat protein produced by wild-type HIV infection. After infection of cells containing the virus with the transdominant tat gene by wild-type HIV, the transdominant protein would likely be induced and wild-type HIV-1 gene expression could potentially be decreased.

HIV proviruses containing the transdominant tat gene in place of tat and the neomycin gene in place of the nef gene have been constructed. This allows the use of G418 selection to identify cells containing mutant viruses. The tat transdominant proviral construct was made as follows. A Stu I linker was inserted into the polylinker of M13 mp19 at nucleotide 6247 (Sma I). An Eco RI (+5287)/Stu I (+6372) fragment from pBH10 (NIH AIDS Reagent Program Catalog #90) was inserted and a stop codon was inserted in the tat gene at amino acid 54 (Dtat) was introduced by site-directed mutagenesis. This mutation does not alter the expression of overlapping gene products. The mutagenized fragment was subcloned into pUC 3' HIV construct containing nucleotide +5219/+9263 (Nco/I/Nar I). A neomycin gene was introduced into this construct. A Bam HI (+8019)/Asp 718 (+8558) fragment from pBH10 was subcloned into mp18 and a Pst I site was introduced at the ATG of the nef coding region by site directed mutagenesis. A Bam HI (+8019)/Xho I (+8443) fragment was inserted into pUC 3' HIV. The neomycin gene from pUC 4k (Pharmacia) was excised as a Pst I fragment and ligated into pUC 3' HIV. Finally a Bgl I/Nco I fragment from pUC 5' HIV was ligated to a Bgl I/Nco I fragment from pUC 3' HIVNEO/Dtat and transfected into 293 cells to generate virus.

A human embryonic kidney cell line, 293 cells, that constitutively produces the adenovirus E1A and E1B proteins, have been demonstrated by the present inventors to induce high level gene expression from tat mutant proviruses. Thus, it is possible to select G418 resistant 293 cell lines containing tat mutants so that viral stocks of high titer can be obtained. These stocks will be used infect H9, Jurkat and U937 cells and G418 resistant cells will be selected. The ability of such cell lines containing transdominant tat mutants to express their gene products will first be determined by addition of wild-type Tat protein to the tissue culture media as described. Both p24 and reverse transcriptase will be assayed to determine if these proviruses are capable of producing high levels of their gene products in the presence of wild-type Tat.

These stable cell lines will then be tested for their ability to be infected with wild-type HIV. Uninfected neomycin resistant cell lines and cell lines containing proviruses with large internal deletions in their tat genes will be used as controls. Monoclonal antibodies directed against the carboxyl terminus of Tat will be used in immunoprecipitation assays to determine the ability of the wild-type virus to infect these cells. Following infection with wild-type virus, p24 and reverse transcriptase assays will be performed. Due to the extremely low expression of these mutant viruses, it is unlikely that they will result in decreased CD4 antigen levels preventing infection by the wild-type virus. Thus, it can be determined whether virus containing the transdominant tat gene can inhibit wild-type HIV gene expression.

The transdominant tat mutant viruses will also be used to infect monocytes, lymphocytes, and peripheral blood lymphocytes previously infected with HIV. This type of experiment may prove difficult because wild-type viral infection may decrease CD4 levels preventing superinfection. PCR analysis of cellular RNA using primers flanking the neomycin gene will be performed to determine if infection by the virus containing the transdominant tat mutant occurs. A reduction in the levels of p24 and reverse transcriptase in response to infection by the transdominant tat mutant virus but not other viruses containing tat deletions will be interpreted to indicate that viruses carrying transdominant tat mutants may inhibit wild-type viral gene expression. These studies will serve as a useful model for the potential development of viruses with anti-viral properties.

EXAMPLE 9

PRODUCTION OF TRANSDOMINANT Tat MUTANT PROTEINS WHICH INHIBIT HIV-1 GENE EXPRESSION

The present example is provided to outline the method which will be employed to demonstrate the production of transdominant tat mutant protein within cell lines.

Several studies indicate that bacterial produced Tat protein is capable of entering cells in culture by endocytosis.[18,23,58] This process is stimulated by the addition of protamine sulfate and inhibited by agents such as heparin.[58] The work of the present inventors has demonstrated that both Tat and a transdominant Tat mutant with a substituted amino acid sequence 52 to 57, tat 52-57, could be produced in bacteria as fusions with the glutathione S-transferase protein.[39] Authentic proteins can be produced following binding of these fusion proteins to glutathione-agarose columns and cleavage of the Tat moiety by treatment with thrombin at a recognition site engineered between the two proteins.

The wild-type Tat protein was greater that 95% pure and bound to TAR RNA with high affinity. The transdominant Tat mutant was also greater than 95% pure but bound poorly to TAR RNA. As a positive control for defective activation of HIV gene expression, a Tat protein with several critical cysteine residues substituted with other amino acids, Δcys, which is known to result in defective activation of HIV gene expression, will also be produced in this bacterial expression system.[11,39]

The ability of either wild-type Tat protein, tat 52-57, or Δcys added to Hela cells to alter gene expression of a transfected HIV LTR CAT construct in both the presence and absence of a tat expression construct will be determined. If no inhibition of Tat activation of the HIV LTR CAT construct is seen with tat 52-57, it will then be determined whether the construct gains entry into the cells and its cytoplasmic and nuclear localization. Either protamine sulfate or heparin will be added with these bacterial synthesized Tat proteins to attempt to alter their cellular uptake as described (Mann, D. A. and Frankel, A. D. (1991), *EMBO J.*, 10:1733–1739). The ability of the tat 52-57 mutant to inhibit HIV-1 gene expression in infected cells will be further investigated. From 1 to 40 mg of either tat 52-57 or Δcys will be added to either HIV-infected Jurkat, H9, or U937 cells every 24 hours. Both p24 and reverse transcriptase assays will be performed to determine the potential role of these Tat proteins on inhibiting HIV-1 gene expression. Tritiated thymidine labeling of cells will be performed to rule out potential toxic effects due to associated contaminant bacterial proteins.

The present inventors believe it is possible that Tat synthesized in bacterial expression systems may not have the same functional activity as similar proteins produced in eucaryotic cells. In addition, bacterial contaminant proteins may prove toxic to cells. To circumvent these problems a wild-type tat and tat mutants tat 52-57 and Δcys will also be produced in eucaryotic cells. A number of viral and cellular proteins have been successfully produced to high levels using vaccinia expression systems. Various tat constructs will be cloned downstream of the T7 promoter in the vaccinia expression vector pTM1. (Elroy-Stein, O., Fuerst, T. R. and Moss, B. (1989), *Proc. Natl. Acad. Sci. USA*, 86:6126–6130). This vector also contains a T7 polymerase terminator sequence and a thymidine kinase gene which undergoes insertional activation upon recombination with wild-type vaccinia virus.

These constructs will be transfected into CV1 cells previously infected with wild-type vaccinia virus and thymidine-kinase negative recombinant virus will be identified following infection of 143 cells. Expression from the recombinant virus will be induced by coinfection with a vaccinia virus containing T7 polymerase. Recently, a modification of this expression system has been used in which an epitope from the influenza hemagglutinin with the amino acid sequence, MYFYDVPDYASLGGP SEQ ID NO: 14 (Field, J. et al. (1988), *Mol. Cell Biol.*, 8:2159–2165), is fused to the protein of interest. A monoclonal antibody known as 12CA5 directed against this epitope sequence binds proteins containing this sequence avidly and peptides corresponding to this sequence can be used to elute epitope-tagged proteins from affinity columns containing these monoclonal antibodies (Field, J. et al. (1988), *Mol. Cell Biol.*, 8:2159–2165). These techniques were used to characterize the human retinoblastoma protein which was expressed in vaccinia and purified by monoclonal antibody affinity chromatography (Templeton, D. (1992), *Mol. Cell Biol.*, 12:435–443). Both wild-type and mutant tat genes will be cloned into vaccinia vectors containing the influenza epitope sequences in their carboxyl terminus to allow synthesis of a Tat-epitope fusion protein. Transfection assays in our laboratory indicate that properties of wild-type tat and transdominant tat genes were not altered when fused with the epitope in their carboxyl terminus.

Recombinant vaccinia viruses will be isolated and dot blot analysis performed to assay for the presence of tat DNA as described (Elroy-Stein et al. (at p. 42)). These recombinant viruses will be used to infect HeLa cells in combination with helper virus encoding T7 polymerase to induce high level expression of the Tat proteins. Whole cell extracts will be prepared from infected HeLa cells and chromatographed on a heparin agarose column using a 0.1 to 1.0M KCL gradient. Fractions from this column will be assayed by Western blot analysis using both influenza epitope monoclonal antibody (Field et al. (at p. 42)) and monoclonal Tat antisera (Modesti, N. et al. (1991), *New Biol.*, 3:759–768). Fractions containing Tat proteins will be bound to a Sepharose column containing influenza epitope monoclonal antibody 12CA5 and eluted using peptide corresponding to the epitope amino acid sequence. Thus, purified Tat proteins can be produced and purified in large quantities from eucaryotic cells using these vaccinia expression system.

Between 1 to 10% of the total cellular protein is frequently the product of cDNAs cloned into vaccinia. Purified wild-type Tat, tat 52-57, and Δcys proteins prepared using vaccinia expression systems will be placed into the tissue culture media and their effects on the expression of HIV LTR CAT reporter constructs transfected into HeLa cells in both the presence and absence of a cotransfected tat gene will be assayed. The effects of these proteins on the expression of HIV-1 in infected cells will also be assayed. These results will be correlated with those obtained using Tat protein from bacterial expression systems. Both vaccinia and bacterial produced Tat proteins will also be assayed using in vitro transcription of the HIV LTR to determine potential differences in their activity (Marciniak, R. A. et al. (1990), *Cell*, 63:791–802) and subjected to structural studies.

Upon identifying transdominant Tat mutants of minimal size using transfection assays with HIV LTR CAT and tat constructs, peptides corresponding to these Tat proteins will be synthesized. Following HPLC purification and amino acid sequence analysis of these peptides, their effects on the expression of HIV LTR CAT constructs and on HIV-1 infected cell lines by addition of the peptides to tissue culture media will be tested. Control peptides will also be used to rule out nonspecific effects of synthesis and purification. This will provide a third method to assay transdominant proteins in an attempt to inhibit HIV-1 gene expression.

EXAMPLE 10

MECHANISMS OF TRANSDOMINANT Tat INHIBITION

The mechanism by which transdominant Tat mutants inhibit wild-type Tat function is not understood. However, several lines of evidence suggest potential mechanisms. For example, immunofluorescence analysis indicates that the transdominant Tat mutant does not prevent the nuclear localization of the wild-type Tat protein. Transdominant Tat mutants are able to inhibit the function of Tat-R17 protein fusions which are capable of activating HIV-1 gene expression via R17 binding sites inserted in place of the TAR element.[63] These results suggest that transdominant mutants do not function by competing with Tat for binding to TAR RNA. The inventors have not yet been able to demonstrate dimerization between Tat and the transdominant Tat mutant. Though none of these results definitively addresses the mechanism of transdominant Tat function, it may be that the transdominant Tat mutants may interact with cellular proteins required for wild-type Tat function. Thus it is important to further investigate the existence of such cellular factors.

Low level expression from stable cell lines containing an integrated tat gene, the quality of Tat antibodies available, and the difficulty of eluting Tat from cells while maintaining interaction with cellular factors have been difficulties associated with determining if cellular factors, such as EIA, tax, and cyclin, directly complex with Tat.

One approach that may solve several of these problems is to infect either HeLa, lymphoid, or monocyte cell lines with vaccinia expression vectors containing either wild-type tat, tat 52-57, or Δcys containing the influenza epitope in their carboxyl terminus and immunoprecipitating Tat and potential associated cellular proteins with monoclonal antibody 12 CA5 directed against the influenza hemagglutinin epitope. From 18 to 24 hours post infection, cells will be labeled with $^{35}$S cysteine and immunoprecipitation will be performed using the monoclonal antibody 12CA5 or an unrelated monoclonal antibody. At these times post-infection inhibition of host protein syntheses is limited. A number of different protocols will be utilized to attempt to identify conditions that result in the elution of Tat from cells, but prevent its potential dissociation from associated cellular factors. This will involve elution with various salt concentrations ranging from 100 mM to 500 mM in both the presence and absence of NP-40. Following immunoprecipitation and autoradiography, the pattern of cellular factors associated with tat, tat 52-57, and Δcys will be compared. Cellular factors in common with wild-type Tat and the transdominant mutant would potentially be targets for involvement in Tat activation.

Next, these associated cellular proteins will be produced in sufficient quantities for further analysis. Large quantities of epitope-tagged Tat can be produced in vaccinia and bound to Sepharose columns containing 12CA5 monoclonal antibody. Following column elution with low concentrations of KCl (0.1M), both Tat and associated cellular proteins will be eluted with increasing KCl concentrations. Associated proteins eluted from this column will be identified by Coomassie staining. The potential role of these proteins in HIV-1 gene expression will be determined by performing gel retardation assays with various HIV LTR DNA and RNA regulatory elements and in vitro transcription assays with the HIV-1 LTR (Marciniak et al. (at p. 44)).

A similar approach to analyze cellular factors that bind to both the Tat protein and the transdominant Tat mutant would be to couple glutathione S-transferase Tat fusion proteins to glutathione-agarose.[39] Nuclear extracts will be chromatographed through these columns, eluted with increasing concentrations of KCl, and analyzed as described above. The pattern of associated cellular proteins will be compared to that obtained from immunoprecipitation of cells infected with vaccinia expression vectors containing tat. Thus we can determine the pattern of cellular factors associated with both Tat and the transdominant Tat mutant. Common factors will be extensively analyzed and potentially preparative scale purification and cloning of the genes encoding these proteins will be performed.

EXAMPLE 11

CONSTRUCTION OF MUTANT TAT HIV RETROVIRAL VECTORS AND INFECTED CELL LINES

The present example is provided to demonstrate one particularly preferred method whereby an HIV vector which includes at least one of the mutant tat genes described herein, such as the tat 52/57 mutant, the tat 54/57 mutant or the tat 55/58 mutant.

Like most retroviruses, the human immunodeficiency virus (HIV) genome encodes two structural genes gag and env, as well as the enzyme reverse transcriptase from the pol gene. In addition, HIV makes the regulatory proteins rev and tat, which are essential for the virus life cycle, and nef which is not essential and acts to reduce virus expression. HIV proviral constructs with tat mutations are extremely defective, producing little or no detectable viral antigen when transfected into the lymphocytic cell lines. Other viral transactivators can stimulate transcription from the HIV LTR independent of tat. These include the E1a and E1b proteins from adenovirus and the immediate early proteins of cytomegalovirus. 293 cells are CD4⁻ human embryonic kidney cells that express E1a and E1b proteins from adenovirus. Early experiments demonstrated that these cells could produce mutated virus but at low levels. The cells produce virus for about two weeks but after a month no viral antigens are detectable. This suggests that 293 cells are not easily reinfected, even cell to cell on plates, and are likely sensitive to the cytopathic effects of HIV. Another possibility is the infected cells do not grow as well as uninfected cells and are eventually diluted from the pool of cells. It is now demonstrated that introducing a drug resistance gene into the HIV genome will overcome these difficulties by selecting for a purified population of cells producing recombinant HIV. The drug resistance genes chosen provide protection against puromycin or G418 and were inserted into HIV at the nef open reading frame.

Pro vital construction

The plasmid pBR322 was cut with Nru I (bp 972) and Cla I (bp23) and endfilled with klenow and religated. This vector was cut with Mro I (bp 1664) and ligated with HIV pro viral DNA which contain nucleotides 359–1455 from ARV-2B, nucleotides 1451–8955 from the HTLV IIIB derivative pBH10, and nucleotides 8920–9475 from ARV-2B. The composite construct produces virus when cut with Mro I and transfected into a number of cell lines including Hela, Jurkat, and 293. Using PCR mutagenesis, a Sma I restriction site was introduced at the initiating ATG of the nef gene of HIV.

```
bp 8847  nef ATG
         aagatgggt gg   SEQ ID NO: 15
         aagatcccggg    SEQ ID NO: 16
              Sma I
```

The puromycin gene was excised as a Hind III/Cla I fragment from the vector pBabepuro and was subcloned in pBKS-. An Eco RV/Xho I fragment from this plasmid was subcloned into the pro viral construct which contains the mutagenized NEF gene. This creates a functional and fully expressed puromycin gene from the HIV LTR. The neomycin gene was excised from the transposon Tn-5 as a Bcl I/Nae I (Partial), endfilled with klenow, and subcloned into the Eco RV site of pBKS-. The Fragment was screened for the desired orientation and excised as a Sma I/Xho I. This fragment was inserted into the pro viral construct containing the mutagenized nef gene. The resulting constructs are pBRHIV-ΔNEF, pBRHIV-puro, and pBRHIV-neo.

Construction of Pro Vital tat Mutant Stop 3

An Eco RI (bp5781)/Asp 718 (bp6390) from pBH10 was subcloned into pUC 19 and used as a template for PCR mutagenesis using the pUC 19 reverse sequencing primer AGCGGATAACAATTTCACACAGGA SEQ ID NO: 17 and the oligomer TCCTATGGCAGGAAGAAGCGGAGATAGTGATGAAGACCTCCTCAA SEQ ID NO: 18
EcoNI.                          stop  stop  stop This mutation does not affect the amino acid sequence of rev in an overlapping reading frame. The PCR product was confirmed by sequencing and subcloned as an EcoNI/Asp 718 fragment into an intermediate containing HIV nucleotides 5781–6641 from pBH10. A Sal I/DraIII fragment from this intermediate was subcloned into pBRHIV-ΔNEF, pBRHIV-puro, and pBRHIV-neo. The new constructs are pBRHIV-ΔNEF/stop3, pBRHIV-puro/stop3, and pBRHIV-neo/stop3.

Production and Analysis of tat Stop3 HIV Virus (1) Transfection and tissue culture techniques.

To produce the mutant tat virus, the proviral constructs pBRHIV-puro/stop3 and pBRHIV-neo/stop3, as well as the corresponding wild type constructs, were cut with the restriction enzyme Mro I and transfected into the human embryonic kidney cell line 293 on 100 mm plates by the calcium phosphate technique. 293 cells were grown and maintained in complete Iscove's supplemented with 5% fetal bovine serum, 5% new born calf serum, penicillin, streptomycin, and gentamicin. The transfected plates were split 48 hours post-transfection 1:20 into media supplemented with either 1.5 ug/ml puromycin or 1.0 mg/ml G418 where appropriate. The cells were fed fresh media every three or four days. In approximately two weeks small cell patches were visualized on the plates and allowed to grow until they became about 3 mm in diameter. Cell foci were removed from the plates with cloning wells and transferred to a 24 well plate. The cells with cloning wells and transferred to a 24 well plate. The cells were allowed to grow to confluence then transferred to a 12 well plate, then to a 60 mm plate and finally to a 100 mm plate.

293 Spinner cell lines were currently under development. The process is similar but cell line are isolated by limiting dilution of a transfected pool of cells.

(2) Analysis of virus production.

A reverse transcription (RT) assay as well as a commercial ELISA assay to the viral antigen p24 (Abbott Laboratories) were used to assay supernatant from the cloned cell lines. 293 cells expressing either HIV-neo or HIV-puro produce 30–250 ng/ml of p24 antigen and from $5 \times 10^5$ cpm/ml to $3 \times 10^6$ cpm/ml RT units of activity. 293 cells expressing either HIV-neo/stop3 or HIV-puro/stop3 produce from 3–30 ng/ml p24 antigen and these supernatants are RT positive. To insure that the mutations were faithfully maintained, two approaches were used to verify the tat stop3 gene. First, chromosomal DNA was isolated from each cloned cell line. Next, oligomer primers which flank the entire first exon of Tat were used to synthesize the Tat gene by PCR. This fragment was cloned into pUC 19 and the entire gene sequenced. A second approach was to isolate a viral pellet, extract the viral RNA, reverse transcribe this RNA and directly sequence tat stop3 using a PCR sequencing technique.

The above-described unique methodologies include the introduction of the Tat and tat mutants into HIV and the successful growth of these viruses on 293 cells. In addition, 293 cells constitute a preferred cell line for the growth of mutant HIV virus, which can then be used for preparing a vaccine according to standard formulation strategies known to those of skill in the medical and pharmaceutical arts (see Remmingtons Pharmaceutical Sciences, 18th edition (1990), specifically incorporated herein by reference in pertinent part).

PROPHETIC EXAMPLE 12

METHODS FOR TREATING HIV-RELATED INFECTIONS IN AN ANIMAL

The present prophetic example is provided to outline a method for using the herein described mutant tat gene containing vectors and/or mutant Tat proteins encoded by the mutant gene, in the treatment of an HIV or HTLV viral infection in an animal, such as a human. Most particularly, the present example outlines a method which may be used in the treatment of humans for the HIV-1 infection known as AIDS. The described methods and therapeutic agents are also contemplated to be effective for the treatment of AIDS related diseases, such as ARC.

To develop transdominant Tat mutant peptides for therapeutic use, it is important to develop transdominant mutants of minimal size, such as the particular substitution mutants and truncated mutants described herein. Minimal size for a proposed peptide mutant is important as the incidence of partial products and yields of peptide is known to decrease significantly as the size of the peptide increases. The minimal size of the claimed transdominant Tat mutant peptides is therefore of advantage in that they provide for both a highly effective and stable product in vivo, as well as for providing for the cost effective efficient production of small peptides.

The basic domain of the Tat protein is known to be critical for nuclear localization and RNA binding,[8,9] and enhances HIV gene expression by binding to a particular bulge region of the TAR RNA, which defines the role of this protein in HIV-1 transactivation. HIV-1 trans-activation is also demonstrated to be critical in HIV gene expression. Therefore, mutation of this basic domain at the particular amino acid residues of the tat gene, as indicated in the foregoing examples, will effectively shut down HIV gene expression. It is contemplated that the information collected by the inventors regarding the effect of various basic domain tat gene mutants on HIV gene expression may be used to develop a vaccine of purified viral antigen which would render animal immunized with the vaccine immune to HIV infection. Specifically, and antigen consisting of a peptide corresponding to the basic domain of the tat gene, specifically at amino residues 49-57, may be employed as part of a vaccine to immunize animals against HIV and AIDS diseases.

Cloned Viral tat DNA

Information generated regarding the effect of mutation of the basic domain of the tat gene (between amino acids 49–57), specifically in the production of tat gene substitution mutants (A-52/57; B-54/57; C-55-58) or truncated mutants (truncated at amino acid 49-53, 55, 56, 57 or 58), may be used to prepare a vaccine useful in the immunization of animal, including humans, against HIV and other HIV-like infections, such as AIDS. Specifically, it is contemplated that the segment of the HIV tat gene corresponding to at least part of the basic domain between amino acids 49–57 may be cloned and used to generate specific, purified HIV Tat basic domain peptide, most preferably as part of an insoluble, fused bacterial-viral protein. Such a fusion protein will then be combined with an effective adjuvant safe and acceptable for use in humans.

The tat gene encoding the basic domain peptide may most preferably be cloned into a prokaryotic cell using a plasmid or bacteriophage vector. Subsequently, the cloned viral DNA for the tat gene basic domain may be expressed as vital protein in either prokaryotic or eukaryotic cells. Most preferably, a eukaryotic cell will be employed to achieve expression of the viral basic domain tat gene.

BIBLIOGRAPHY

The following references are specifically incorporated herein by reference for the purposes indicated.
1. Berkhout, B. and Jeang, K. T. (1989) *J. Virol.*, 63:5501–5504.
2. Berhkout, B. et al. (1989) *Cell*, 59:273–282.
3. Brake, D. A. et al. (1990) *J. Virol.*, 64:962–965.
4. Calnan, B. J. et al. (1991) *Genes Dev.*, 5:201–210.
5. Dayton, A. I. et al. (1986) *Cell*, 44:941–947.
6. Dingwall, C. et al. (1986) *EMBO J*, 9:4145–4153.
7. Feng, S. and Holland, E. C. (1988) *Nature*, 334:165–167.
8. Fisher, A. G. et al. (1986) *Nature*, 320:367–371.
9. Frankel, A. D. et al. (1988) *Science*, 240:70–73.
10. Friedman, A. D. et al. (1988) *Nature*, 335:452–454.
11. Garcia, J. A. et al. (1988) *EMBO J*, 7:3143–3147.
12. Garcia, J. A. et al. (1989) *EMBO J*, 8:765–778.
13. Glen, G. M. and Ricciardi, R. P. (1987) *Mol Cell Biol*, 7:1004–1010.
14. Gorman, C. M. et al. (1982) *Mol Cel Biol*, 2:1044–1051.
15. Harrich, D. et al. (1990) *EMBO J*, 9:4417–4424.
16. Hauber, J. et al. (1987) *Proc Natl Acad Sci. USA*, 84:6364–6368.
17. Hauber, J. et al. (1989) *J. Virol*, 63:1181–1187.
18. Jones, K. A. et al. (1986) *Science*, 232:755–759.
19. Malim et al. (1989) *Cell*, 58:205–214.
20. Nabel, G. and Baltimore, D. (1987) *Nature*, 326:711–713.
21. Pearson, L. et al. (1990) *Proc. Natl. Acad. Sci., USA*, 87:5079–5083.
22. Rappaport, J. et al. (1989) *New Biol.*, 1:101:110.
23. Rice, A. P. and Carlotti, F. (1990) *J. Virol.*, 64:1864–1868.
24. Rosen, C. A. et al. (1985) *Cell*, 41:813:823.
25. Roy, S. et al. (1990a) *J. Virol.*, 64:1402–1406.
26. Roy, S. et al. (1990b) *Genes. Dev.*, 4:1365–1373.
27. Ruben, S. et al. (1989) *J. Virol.*, 63:–8.
28. Sadaie, M. R. et al. (1988) *Science*, 239:910–913.
29. Selby, M. J. and Peterlin, B. M. (1990) *Cell*, 62:769–776.
30. Selby, M. J. et al. (1989) *Genes Dev.*, 3:547–558.
31. Siomi, H. et al. (1990) *J. Virol.*, 64: 1803–1807.
32. Sodroski, J. et al. (1985) *Science*, 227:171–173.
33. Trono, D. et al. (1989) *Cell*, 59:113–120.
34. Wachsman, W. et al. (1987) *Science*, 235: 674–677.
35. Weeks, K. M. et al. (1990) *Science*, 249:1281–1285.
36. Wright, C. M. et al. (1986) *Science*, 234:988–992.
37. Remmingtons Pharmaceutical Science (1990) 18th edition, Mack Publishing Company, Easton, Pa., A. Gennaro, editor.
38. Gentz, R., Chen, C. H. and Rosen, C. A. *Proc. Natl. Acad. Sci. USA*, 86:821–824.
39. Wu, F. et al. (1991) *Genes Dev.*, 5:2128–2140.
40. Morganstern, J. P. and Land, H. (1990) *Nucl. Acids Res.*, 18:3587–3596.

41. Mann, D. A. and Frankel, A. D. (1991) *EMBO J.*, 10:1733–1739.
42. Elroy-Stein, O. et al. (1989) *Proc. Natl. Acad. Sci. USA*, 86:6126–6130.
43. Field, J. et al. (1988) *Mol. Cell, Biol.*, 8:2159–2169.
44. Templeton, D. (1992) *Mol. Cell. Biol.*, 12:435–443.
45. Modesti, N. et al. (1991) *New Biol.*, 3:759–768.
46. Marciniak, R. A. et al. (1990) *Cell*, 63:791–802.

What is claimed is:

1. A transdominant mutant HIV Tat protein, the protein inhibiting HIV gene expression in the presence of an equimolar concentration of wild-type Tat protein and being encoded by a substitution mutant tat gene having a substituted basic domain in which more than two positively-charged amino acids are replaced by neutral amino acids.

2. The transdominant mutant HIV Tat protein of claim 1 wherein the amino acid sequence includes an amino acid substitution of glycine or alanine in place of arginine or lysine in the basic domain.

3. The transdominant mutant HIV Tat protein of claim 1 further defined as a fusion protein.

4. The transdominant mutant HIV Tat protein of claim 1 wherein the substituted mutant tat gene encoding said mutant Tat protein includes a sequence corresponding to SEQ ID NO: 19, SEQ ID NO: 21 or SEQ ID NO: 22.

5. The transdominant mutant HIV Tat protein of claim 1 wherein the protein includes a substituted basic domain in which 4 or 6 positively-charged amino acids are replaced by neutral amino acids.

6. A transdomiant mutant HIV Tat protein encoded by a substitution mutant tat gene wherein the substitution mutant tat gene is defined as a tat 52/57 mutant, a tat 55/58 mutant, or a tat 54/57 mutant.

7. The transdominant mutant HIV Tat protein of claim 6 wherein the tat 52/57 mutant includes a nucleotide sequence which encodes an amino acid sequence Gly-Gly-Ala-Gly-Gly-Gly SEQ ID NO: 4 at amino acids 52 through 57 of the mutant Tat protein.

8. The transdominant mutant HIV Tat protein of claim 6 wherein the tat 54/57 mutant includes a nucleotide sequence which encodes an amino acid sequence Ala-Gly-Gly-Gly SEQ ID NO: 6 at amino acids 54 through 57 of the mutant Tat protein.

9. The transdominant mutant HIV Tat protein of claim 6 wherein the tat 55/58 mutant includes a sequence which encodes an amino acid sequence Gly-Ala-Gly-Gly SEQ ID NO: 7 at amino acids 55 through 58 of the mutant Tat protein.

10. The transdominant mutant HIV Tat protein of claim 6 wherein the substitution mutant tat gene is present within an expression vector.

11. The transdominant mutant Tat protein of claim 10 wherein the expression vector is an SV40 or CMV expression vector.

* * * * *

UNITED STATES PATENT AND TRADEMARK OFFICE
CERTIFICATE OF CORRECTION

PATENT NO. : 5,597,895
DATED : January 28, 1997
INVENTOR(S) : Richard B. Gaynor, et al It is certified that error appears in the above-indentified patent and that said Letters Patent is hereby corrected as shown below:

In claim 1, column 39, line 4, delete "tat" and substitute --*tat*--, therefor.

In claim 4, column 39, line 2, delete "tat" and substitute --*tat*--, therefor.

In claim 6 column 39, lines 2-4, delete all occurrences of "tat" and substitute --*tat*--, therefor.

In claim 7, column 40, line 2, delete "tat" and substitute --*tat*--, therefor.

In claim 8, column 40, line 2, delete "tat" and substitute --*tat*--, therefor.

In claim 9, column 40, line 2, delete "tat" and substitute --*tat*--, therefor.

In claim 10, column 40, line 10, delete "tat" and substitute --*tat*--, therefor.

Signed and Sealed this

Twenty-ninth Day of April, 1997

*Attest:*

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met Glu Pro Val Asp Pro Asn Leu Glu Pro Trp Lys His Pro Gly Ser
 1               5                  10                  15
Gln Pro Arg Thr Ala Cys Asn Asn Cys Tyr Cys Lys Lys Cys Cys Phe
            20                  25                  30
His Cys Tyr Ala Cys Phe Thr Arg Lys Gly Leu Gly Ile Ser Tyr Gly
        35                  40                  45
Arg Lys Lys Gly Gly Ala Gly Gly Ala Pro Gln Asp Ser Gln Thr
    50                  55                  60
His Gln Ala Ser Leu Ser Lys Gln
65                  70
```

( 2 ) INFORMATION FOR SEQ ID NO:2:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Glu Pro Val Asp Pro Asn Leu Glu Pro Trp Lys His Pro Gly Ser
 1               5                  10                  15
Gln Pro Arg Thr Ala Cys Asn Asn Cys Tyr Cys Lys Lys Cys Cys Phe
            20                  25                  30
His Cys Tyr Ala Cys Phe Thr Arg Lys Gly Leu Gly Ile Ser Tyr Gly
        35                  40                  45
Arg Lys Lys Arg Arg Gln Arg Arg Ala Pro Gln Asp Ser Gln Thr
    50                  55                  60
His Gln Ala Ser Leu Ser Lys Gln
65                  70
```

( 2 ) INFORMATION FOR SEQ ID NO:3:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
         Met  Glu  Pro  Val  Asp  Pro  Asn  Leu  Glu  Pro  Trp  Lys  His  Pro  Gly  Ser
         1              5                        10                            15

Gln  Pro  Arg  Thr  Ala  Cys  Asn  Asn  Cys  Tyr  Cys  Lys  Lys  Cys  Cys  Phe
                        20                       25                       30

His  Cys  Tyr  Ala  Cys  Phe  Thr  Arg  Lys  Gly  Leu  Gly  Ile  Ser  Tyr  Gly
                   35                       40                       45

Arg  Lys  Lys  Arg  Arg  Ala  Gly  Gly  Ala  Pro  Gln  Asp  Ser  Gln  Thr
              50                       55                       60

His  Gln  Ala  Ser  Leu  Ser  Lys  Gln
         65                       70
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
         Gly  Gly  Ala  Gly  Gly  Gly
         1                   5
```

( 2 ) INFORMATION FOR SEQ ID NO:5:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
         Met  Glu  Pro  Val  Asp  Pro  Asn  Leu  Glu  Pro  Trp  Lys  His  Pro  Gly  Ser
         1              5                        10                            15

Gln  Pro  Arg  Thr  Ala  Cys  Asn  Asn  Cys  Tyr  Cys  Lys  Lys  Cys  Cys  Phe
                        20                       25                       30

His  Cys  Tyr  Ala  Cys  Phe  Thr  Arg  Lys  Gly  Leu  Gly  Ile  Ser  Tyr  Gly
                   35                       40                       45

Arg  Lys  Lys  Arg  Arg  Gln  Gly  Ala  Gly  Gly  Pro  Gln  Asp  Ser  Gln  Thr
              50                       55                       60

His  Gln  Ala  Ser  Leu  Ser  Lys  Gln
         65                       70
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
         Ala  Gly  Gly  Gly
         1
```

( 2 ) INFORMATION FOR SEQ ID NO:7:

( i ) SEQUENCE CHARACTERISTICS:

(A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gly Ala Gly Gly
    1

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Arg Arg Gln Arg Arg Arg
    1               5

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:9:

GGGGGAGCCG GCGGAGGA                                             18

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gln Arg Arg Arg
    1

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:11:

GCCGGCGGAG GA                                                   12

(2) INFORMATION FOR SEQ ID NO:12:

(i) SEQUENCE CHARACTERISTICS:

(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Arg Arg Arg Ala
1

(2) INFORMATION FOR SEQ ID NO:13:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:13:

GGAGCCGGCG GT                                                                  12

(2) INFORMATION FOR SEQ ID NO:14:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:14:

Met Tyr Phe Tyr Asp Val Pro Asp Tyr Ala Ser Leu Gly Gly Pro
1               5                   10                  15

(2) INFORMATION FOR SEQ ID NO:15:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:15:

AAGATGGGTG G                                                                   11

(2) INFORMATION FOR SEQ ID NO:16:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:16:

AAGATCCCGG G                                                                   11

(2) INFORMATION FOR SEQ ID NO:17:

(i) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:17:

AGCGGATAAC AATTTCACAC AGGA                                        24

(2) INFORMATION FOR SEQ ID NO:18:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:18:

TCCTATGGCA GGAAGAAGCG GAGATAGTGA TGAAGACCTC CTCAA                  45

(2) INFORMATION FOR SEQ ID NO:19:

(i) SEQUENCE CHARACTERISTICS:
(A) LENGTH: 219 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:19:

ATGGAGCCAG TAGATCCTAA TCTAGAGCCC TGGAAGCATC CAGGAAGTCA GCCTAGGACT     60

GCTTGTAACA ATTGCTATTG TAAAAAGTGT TGCTTTCATT GCTACGCGTG TTTCACAAGA    120

AAAGGCTTAG GCATCTCCTA TGGCAGGAAG AAGGGGGGAG CCGGCGGAGG AGCTCCTCAG    180

GACAGTCAGA CTCATCAAGC TTCTCTATCA AAGCAGTAA                           219

(2) INFORMATION FOR SEQ ID NO:20:

(i) SEQUENCE CHARACTERISTICS:
(A) LENGTH: 219 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="DNA"

(xi) SEQUENCE DESCRIPTION: SEQ ID NO:20:

ATGGAGCCAG TAGATCCTAA TCTAGAGCCC TGGAAGCATC CAGGAAGTCA GCCTAGGACT     60

GCTTGTAACA ATTGCTATTG TAAAAAGTGT TGCTTTCATT GCTACGCGTG TTTCACAAGA    120

AAAGGCTTAG GCATCTCCTA TGGCAGGAAG AAGCGGAGAC AGCGACGAAG AGCTCCTCAG    180

GACAGTCAGA CTCATCAAGC TTCTCTATCA AAGCAGTAA                           219

(2) INFORMATION FOR SEQ ID NO:21:

(i) SEQUENCE CHARACTERISTICS:
(A) LENGTH: 219 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="DNA"

(x i) SEQUENCE DESCRIPTION: SEQ ID NO:21:

| ATGGAGCCAG | TAGATCCTAA | TCTAGAGCCC | TGGAAGCATC | CAGGAAGTCA | GCCTAGGACT | 60 |
| GCTTGTAACA | ATTGCTATTG | TAAAAAGTGT | TGCTTTCATT | GCTACGCGTG | TTTCACAAGA | 120 |
| AAAGGCTTAG | GCATCTCCTA | TGGCAGGAAG | AAGCGGAGAG | CCGGCGGAGG | AGCTCCTCAG | 180 |
| GACAGTCAGA | CTCATCAAGC | TTCTCTATCA | AAGCAGTAA | | | 219 |

(2) INFORMATION FOR SEQ ID NO:22:

(i) SEQUENCE CHARACTERISTICS:
(A) LENGTH: 219 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="DNA"

(x i) SEQUENCE DESCRIPTION: SEQ ID NO:22:

| ATGGAGCCAG | TAGATCCTAA | TCTAGAGCCC | TGGAAGCATC | CAGGAAGTCA | GCCTAGGACT | 60 |
| GCTTGTAACA | ATTGCTATTG | TAAAAAGTGT | TGCTTTCATT | GCTACGCGTG | TTTCACAAGA | 120 |
| AAAGGCTTAG | GCATCTCCTA | TGGCAGGAAG | AAGCGGAGAC | AGGGAGCCGG | CGGTCCTCAG | 180 |
| GACAGTCAGA | CTCATCAAGC | TTCTCTATCA | AAGCAGTAA | | | 219 |